United States Patent
Limem et al.

(10) Patent No.: US 11,779,455 B2
(45) Date of Patent: Oct. 10, 2023

(54) MEDICAL DEVICES TO LIMIT MOVEMENT OF BREAST IMPLANTS

(71) Applicant: Tepha, Inc., Lexington, MA (US)

(72) Inventors: Skander Limem, Melrose, MA (US); Kristin Crescenzi, Sudbury, MA (US); Said Rizk, Windham, NH (US); Simon F. Williams, Lexington, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 16/587,903

(22) Filed: Sep. 30, 2019

(65) Prior Publication Data
US 2020/0100892 A1 Apr. 2, 2020

Related U.S. Application Data

(60) Provisional application No. 62/868,298, filed on Jun. 28, 2019, provisional application No. 62/740,146, filed on Oct. 2, 2018.

(51) Int. Cl.
*A61F 2/12* (2006.01)
*A61F 2/00* (2006.01)

(52) U.S. Cl.
CPC ........ *A61F 2/12* (2013.01); *A61F 2002/0081* (2013.01); *A61F 2210/0004* (2013.01);
(Continued)

(58) Field of Classification Search
CPC ............... A61F 2/12; A61F 2002/0081; A61F 2210/0076; A61F 2220/0008;
(Continued)

(56) References Cited

U.S. PATENT DOCUMENTS

| | | |
|---|---|---|
| 2,701,879 A | 2/1955 | Bennett |
| 3,280,818 A | 10/1966 | Pankey et al. |

(Continued)

FOREIGN PATENT DOCUMENTS

| | | |
|---|---|---|
| CA | 2829201 A1 | 9/2012 |
| EP | 1940312 B1 | 7/2009 |

(Continued)

OTHER PUBLICATIONS

U.S. Appl. No. 29/668,175, filed Oct. 25, 1966, Pankey et al.
(Continued)

*Primary Examiner* — Yashita Sharma
(74) *Attorney, Agent, or Firm* — Wolf, Greenfield & Sacks, P.C.

(57) ABSTRACT

Breast fixation devices for use in breast reconstruction and breast augmentation limit the rotation or movement of breast implants after implantation that results in an unnatural appearance of the breast. The breast fixation devices can include a thin-walled enclosure in the shape of a pouch. A breast implant is secured inside the pouch to limit movement by applying compression to the breast implants, or using a mating or interlocking mechanism between the pouch and breast implant. The pouches containing the breast implants are implanted in the breast. Tissue in-growth into the pouch limits movement of the pouch-breast implant assembly and thereby limits rotation, migration, and displacement of the breast implant. The pouches preferably comprise poly-4-hydroxybutyrate or copolymer thereof.

21 Claims, 16 Drawing Sheets

(52) U.S. Cl.
CPC ............... A61F 2210/0076 (2013.01); A61F 2220/0008 (2013.01); A61F 2240/001 (2013.01); A61F 2250/0018 (2013.01); A61F 2250/0036 (2013.01); A61F 2250/0067 (2013.01)

(58) Field of Classification Search
CPC ........ A61F 2240/001; A61F 2250/0067; A61F 2250/0018; A61F 2250/0036; A61F 2210/0004; A61F 2002/0086; A61F 2220/0075; A61F 2220/0016; A61F 2220/0058; A61F 2002/0068; A61F 2250/0023; A61F 2250/003; A61F 2/0063; A61L 27/18; A61L 2430/04; A61L 27/58
See application file for complete search history.

(56) References Cited

U.S. PATENT DOCUMENTS

| | | | |
|---|---|---|---|
| 3,293,663 | A | 12/1966 | Cronin |
| 3,366,975 | A * | 2/1968 | Pangman ................ A61F 2/12 623/8 |
| 3,934,593 | A | 1/1976 | Mellinger |
| 4,372,293 | A | 2/1983 | Vijil-Rosales |
| 4,380,569 | A | 4/1983 | Shaw |
| 4,388,735 | A | 6/1983 | Ionescu et al. |
| 4,773,909 | A | 9/1988 | Chaglassian |
| 4,801,299 | A | 1/1989 | Brendel et al. |
| 4,863,470 | A | 9/1989 | Carter |
| 4,936,858 | A | 6/1990 | O'Keeffe |
| 4,960,425 | A | 10/1990 | Yan et al. |
| 5,007,929 | A | 4/1991 | Quaid |
| 5,011,494 | A | 4/1991 | von Recum et al. |
| 5,217,494 | A | 6/1993 | Coggins et al. |
| 5,356,429 | A | 10/1994 | Seare |
| 5,383,929 | A | 1/1995 | Ledergerber |
| 5,480,430 | A | 1/1996 | Carlisle et al. |
| 5,500,019 | A | 3/1996 | Johnson et al. |
| 5,545,221 | A | 8/1996 | Hang-Fu |
| 5,584,884 | A | 12/1996 | Pignataro |
| 5,658,328 | A | 8/1997 | Johnson |
| 5,658,329 | A | 8/1997 | Purkait |
| 5,676,161 | A | 10/1997 | Breiner |
| 5,716,404 | A | 2/1998 | Vacanti et al. |
| 5,755,611 | A | 5/1998 | Noble et al. |
| 5,759,204 | A | 6/1998 | Seare |
| 5,902,335 | A | 5/1999 | Snyder, Jr. |
| 5,990,378 | A | 11/1999 | Ellis |
| 6,074,421 | A | 6/2000 | Murphy |
| 6,113,634 | A | 9/2000 | Weber-Unger et al. |
| 6,146,418 | A * | 11/2000 | Berman ................ A61M 31/00 623/7 |
| 6,210,439 | B1 | 4/2001 | Firmin et al. |
| 6,328,765 | B1 | 12/2001 | Hardwick et al. |
| 6,368,541 | B1 | 4/2002 | Pajotin et al. |
| 6,371,831 | B1 | 4/2002 | Dodge |
| 6,544,287 | B1 | 4/2003 | Johnson et al. |
| 6,599,323 | B2 | 7/2003 | Melican et al. |
| 6,682,559 | B2 | 1/2004 | Myers et al. |
| 6,723,133 | B1 | 4/2004 | Pajotin |
| 6,740,122 | B1 | 5/2004 | Pajotin |
| 6,913,626 | B2 | 7/2005 | Mcghan |
| 7,081,135 | B2 | 7/2006 | Smith et al. |
| D539,506 | S | 4/2007 | Valentin |
| 7,476,249 | B2 | 1/2009 | Frank |
| 7,520,896 | B2 | 4/2009 | Benslimane |
| 7,670,372 | B2 | 3/2010 | Shfaram et al. |
| 7,875,074 | B2 | 1/2011 | Chen et al. |
| 7,998,202 | B2 | 8/2011 | Lesh |
| 8,007,531 | B2 | 8/2011 | Frank |
| 8,034,270 | B2 | 10/2011 | Martin et al. |
| 8,043,373 | B2 | 10/2011 | Schuessler et al. |
| 8,101,116 | B2 | 1/2012 | Lindh, Sr. et al. |
| 8,211,173 | B2 | 7/2012 | Keller et al. |
| 8,377,127 | B2 | 2/2013 | Schuessler |
| 8,506,582 | B2 | 8/2013 | Kammerer et al. |
| 8,728,159 | B2 | 5/2014 | Kim et al. |
| 8,778,020 | B2 | 7/2014 | Gregg et al. |
| 8,858,629 | B2 | 10/2014 | Moses et al. |
| 8,911,765 | B2 | 12/2014 | Moses et al. |
| 8,936,504 | B2 | 1/2015 | Deal et al. |
| 8,986,377 | B2 | 3/2015 | Richter et al. |
| 9,277,986 | B2 | 3/2016 | Moses et al. |
| 9,474,598 | B2 | 10/2016 | Gregg et al. |
| 9,532,867 | B2 | 1/2017 | Felix et al. |
| 9,555,155 | B2 | 1/2017 | Ganatra et al. |
| 9,585,744 | B2 | 3/2017 | Moses et al. |
| 9,603,698 | B2 | 3/2017 | Kerr et al. |
| 9,636,211 | B2 | 5/2017 | Felix et al. |
| 9,655,715 | B2 | 5/2017 | Limem et al. |
| 9,700,411 | B2 | 7/2017 | Klima et al. |
| 9,707,073 | B2 | 7/2017 | Al-Jasim |
| 9,713,350 | B1 | 7/2017 | Colburn |
| 9,713,524 | B2 * | 7/2017 | Glicksman ............ A61B 90/90 |
| D799,152 | S | 10/2017 | Brownell et al. |
| D803,401 | S | 11/2017 | Limem et al. |
| D816,220 | S | 4/2018 | Limem et al. |
| D816,221 | S | 4/2018 | Limem et al. |
| 10,028,818 | B2 | 7/2018 | Felix et al. |
| 10,052,192 | B2 | 8/2018 | Schuessler et al. |
| 10,058,417 | B2 | 8/2018 | Limem et al. |
| D836,778 | S | 12/2018 | Limem et al. |
| 10,258,460 | B2 | 4/2019 | Moses et al. |
| 10,363,127 | B2 | 7/2019 | Mlodinow et al. |
| D856,517 | S | 8/2019 | Spiegel et al. |
| D857,895 | S | 8/2019 | Limem et al. |
| 10,405,969 | B2 | 9/2019 | Bertoli et al. |
| 10,449,034 | B2 | 10/2019 | Bowley et al. |
| D870,289 | S | 12/2019 | Limem et al. |
| 10,568,728 | B2 | 2/2020 | Felix et al. |
| 10,595,986 | B2 | 3/2020 | Rehnke |
| D888,244 | S | 6/2020 | Limem et al. |
| 10,695,165 | B2 | 6/2020 | Shetty et al. |
| D889,654 | S | 7/2020 | Limem et al. |
| D889,655 | S | 7/2020 | Limem et al. |
| 10,722,345 | B2 | 7/2020 | Limem et al. |
| D892,329 | S | 8/2020 | Limem et al. |
| D894,393 | S | 8/2020 | Limem et al. |
| D896,383 | S | 9/2020 | Schuessler et al. |
| 10,765,507 | B2 | 9/2020 | Moses et al. |
| D926,984 | S | 8/2021 | Schuessler et al. |
| D927,690 | S | 8/2021 | Limem et al. |
| 11,154,393 | B2 | 10/2021 | Limem et al. |
| D956,977 | S | 7/2022 | Limem et al. |
| 2002/0022883 | A1 | 2/2002 | Burg |
| 2002/0143396 | A1 | 10/2002 | Falcon et al. |
| 2002/0165596 | A1 | 11/2002 | Wilson |
| 2003/0195620 | A1 | 10/2003 | Huynh et al. |
| 2003/0207649 | A1 | 11/2003 | Reeder |
| 2003/0212461 | A1 | 11/2003 | Vadurro et al. |
| 2003/0212462 | A1 | 11/2003 | Gryska et al. |
| 2004/0225352 | A1 | 11/2004 | Osborne et al. |
| 2005/0027348 | A1 | 2/2005 | Case et al. |
| 2006/0167338 | A1 | 7/2006 | Shfaram et al. |
| 2006/0211334 | A1 | 9/2006 | Smith |
| 2007/0055371 | A1 * | 3/2007 | Laghi .................. A61F 2/52 450/55 |
| 2007/0088434 | A1 | 4/2007 | Frank |
| 2007/0135929 | A1 | 6/2007 | Williams et al. |
| 2007/0196421 | A1 | 8/2007 | Hunter et al. |
| 2007/0198085 | A1 | 8/2007 | Benslimane |
| 2008/0027273 | A1 | 1/2008 | Gutterman |
| 2008/0082113 | A1 | 4/2008 | Bishop et al. |
| 2008/0097601 | A1 | 4/2008 | Codori-Hurff et al. |
| 2008/0128315 | A1 | 6/2008 | Buevich et al. |
| 2008/0154366 | A1 | 6/2008 | Frank |
| 2008/0241212 | A1 * | 10/2008 | Moses .................. A61K 31/65 424/423 |
| 2009/0082864 | A1 | 3/2009 | Chen et al. |
| 2009/0240342 | A1 | 9/2009 | Lindh, Sr. et al. |
| 2009/0248071 | A1 | 10/2009 | Saint et al. |
| 2010/0021738 | A1 | 1/2010 | Maida et al. |

(56) References Cited

U.S. PATENT DOCUMENTS

| | | |
|---|---|---|
| 2010/0023120 A1 | 1/2010 | Holecek et al. |
| 2010/0030015 A1 | 2/2010 | Delorme et al. |
| 2010/0042211 A1 | 2/2010 | Epps et al. |
| 2010/0137679 A1 | 6/2010 | Lashinski et al. |
| 2010/0191330 A1 | 7/2010 | Lauryssen et al. |
| 2010/0204791 A1 | 8/2010 | Shfaram et al. |
| 2010/0217388 A1 | 8/2010 | Cohen et al. |
| 2010/0249924 A1 | 9/2010 | Powell et al. |
| 2010/0249947 A1 | 9/2010 | Lesh et al. |
| 2010/0305696 A1 | 12/2010 | Mao et al. |
| 2010/0331612 A1 | 12/2010 | Lashinski et al. |
| 2011/0009960 A1 | 1/2011 | Altman et al. |
| 2011/0022171 A1 | 1/2011 | Richter et al. |
| 2011/0257665 A1 | 10/2011 | Mortarino |
| 2011/0264213 A1 | 10/2011 | DeMiranda |
| 2011/0276122 A1 | 11/2011 | Schlick et al. |
| 2011/0301706 A1 | 12/2011 | Brooks et al. |
| 2012/0004723 A1 | 1/2012 | Mortarino et al. |
| 2012/0021738 A1 | 1/2012 | Koo et al. |
| 2012/0022646 A1 | 1/2012 | Mortarino et al. |
| 2012/0158134 A1 | 6/2012 | Codori-Hurff et al. |
| 2012/0185041 A1 | 7/2012 | Mortarino et al. |
| 2012/0221105 A1 | 8/2012 | Altman et al. |
| 2012/0226352 A1 | 9/2012 | Becker |
| 2012/0232653 A1 | 9/2012 | Saint et al. |
| 2012/0266348 A1 | 10/2012 | Meginnis |
| 2012/0283826 A1 | 11/2012 | Moses et al. |
| 2013/0066423 A1 | 3/2013 | Bishop et al. |
| 2013/0103149 A1 | 4/2013 | Altman et al. |
| 2013/0116778 A1 | 5/2013 | Gregg et al. |
| 2013/0178699 A1 | 7/2013 | Saint et al. |
| 2013/0178875 A1 | 7/2013 | Horton et al. |
| 2013/0253645 A1 | 9/2013 | Kerr et al. |
| 2013/0304098 A1 | 11/2013 | Mortarino |
| 2014/0017284 A1 | 1/2014 | Yang et al. |
| 2014/0046442 A1 | 2/2014 | Guterman |
| 2014/0081398 A1 | 3/2014 | Mejia et al. |
| 2014/0135925 A1 | 5/2014 | Brooks et al. |
| 2014/0163696 A1 | 6/2014 | Lesh et al. |
| 2014/0200396 A1 | 7/2014 | Lashinski et al. |
| 2014/0222146 A1 | 8/2014 | Moses et al. |
| 2014/0222161 A1 | 8/2014 | Mathisen |
| 2014/0257482 A1 | 9/2014 | Ward et al. |
| 2014/0276993 A1 | 9/2014 | Reilly et al. |
| 2014/0276997 A1 | 9/2014 | Harrah et al. |
| 2015/0012089 A1 | 1/2015 | Shetty et al. |
| 2015/0018946 A1 | 1/2015 | Guterman |
| 2015/0056131 A1 | 2/2015 | Bernasconi et al. |
| 2015/0081000 A1 | 3/2015 | Hossainy et al. |
| 2015/0112434 A1 | 4/2015 | Felix et al. |
| 2015/0134043 A1 | 5/2015 | Irwin et al. |
| 2015/0223928 A1 | 8/2015 | Limem et al. |
| 2015/0272722 A1 | 10/2015 | Davila et al. |
| 2015/0351889 A1 | 12/2015 | Reddy et al. |
| 2015/0351891 A1 | 12/2015 | Moses et al. |
| 2015/0351899 A1 | 12/2015 | Mortarino |
| 2015/0351900 A1* | 12/2015 | Glicksman ............. A61B 90/02 623/8 |
| 2016/0022416 A1 | 1/2016 | Felix et al. |
| 2016/0038269 A1 | 2/2016 | Altman et al. |
| 2016/0106538 A1 | 4/2016 | Mitra et al. |
| 2016/0151062 A1 | 6/2016 | Bachrach |
| 2016/0151138 A1 | 6/2016 | Guterman et al. |
| 2016/0166727 A1* | 6/2016 | Ganatra ................... D04C 1/12 424/1.11 |
| 2016/0256268 A1 | 9/2016 | Dakin |
| 2016/0296329 A1 | 10/2016 | Alkhatib et al. |
| 2016/0310262 A1* | 10/2016 | Doucet .................... A61F 2/12 |
| 2017/0014226 A1 | 1/2017 | Fenaroli |
| 2017/0065403 A1 | 3/2017 | Al-Jasim |
| 2017/0143475 A1 | 5/2017 | Moses et al. |
| 2017/0196672 A1 | 7/2017 | Guterman |
| 2017/0216009 A1 | 8/2017 | Felix et al. |
| 2017/0216018 A1 | 8/2017 | Limem et al. |
| 2017/0224471 A1 | 8/2017 | Rehnke |
| 2018/0055624 A1 | 3/2018 | Barere et al. |
| 2018/0303599 A1 | 10/2018 | Al-Jasim |
| 2018/0325644 A1 | 11/2018 | Felix et al. |
| 2019/0216595 A1 | 7/2019 | Moses et al. |
| 2019/0247180 A1 | 8/2019 | Limem et al. |
| 2019/0254807 A1 | 8/2019 | Limem et al. |
| 2020/0085526 A1* | 3/2020 | Schuessler ............. A61B 90/02 |
| 2020/0261202 A1 | 8/2020 | Mathisen et al. |
| 2020/0276006 A1 | 9/2020 | Felix et al. |
| 2020/0360129 A1 | 11/2020 | Moses et al. |
| 2020/0397554 A1 | 12/2020 | Epps et al. |
| 2020/0405473 A1 | 12/2020 | Nanni |
| 2021/0069374 A1 | 3/2021 | Brennan et al. |
| 2021/0153997 A1 | 5/2021 | Limem et al. |
| 2021/0251738 A1 | 8/2021 | Young |
| 2022/0079741 A1 | 3/2022 | Limem et al. |
| 2022/0079742 A1 | 3/2022 | Limem et al. |

FOREIGN PATENT DOCUMENTS

| | | | |
|---|---|---|---|
| EP | | 2903563 A1 | 8/2015 |
| EP | | 2903563 B1 | 11/2017 |
| EP | | 2190382 B1 | 10/2018 |
| EP | | 19869949.8 | 5/2022 |
| JP | | 2004-130118 A | 4/2004 |
| JP | | 4296399 B2 | 7/2009 |
| WO | | 2004096098 A1 | 11/2004 |
| WO | | 2006117622 A1 | 11/2006 |
| WO | | 2007004214 A3 | 5/2007 |
| WO | | 2009001293 A1 | 12/2008 |
| WO | | 2009050706 A2 | 4/2009 |
| WO | | 2011119742 A2 | 9/2011 |
| WO | | 2012012215 A2 | 1/2012 |
| WO | | 2012122215 A2 | 9/2012 |
| WO | WO | 2014/041577 A1 | 3/2014 |
| WO | | 2015006737 A1 | 1/2015 |
| WO | | 2019094861 A1 | 5/2019 |
| WO | | 2019119060 A1 | 6/2019 |
| WO | | 2019175911 A2 | 9/2019 |
| WO | WO | 2019/243599 A1 | 12/2019 |
| WO | | 2020070694 A1 | 4/2020 |
| WO | | 2020072349 A1 | 4/2020 |
| WO | | 2020242694 A1 | 12/2020 |
| WO | | 2021015976 A1 | 1/2021 |
| WO | | 2021022484 A1 | 2/2021 |
| WO | | 2021063850 A1 | 4/2021 |
| WO | | 2021063851 A1 | 4/2021 |

OTHER PUBLICATIONS

"GalaFLEX Mesh . . . Supporting Your Quest for Timeless Beauty," Tepha, Inc. 400109 Rev.B, Oct. 2012.

"GalaFLEX Mesh," Tepha Inc., www.galateasurgical.com, P/N 400124, Rev.A, Oct. 2013.

Auclair, et al, "Repair of mammary ptosis by insertion of an internal absorbable support and periareaolar scar," Ann Chir Plast Esthet, 1993, 38, No. 1, pp. 107-113.

Bertozzi, N. Ann Med Surg. 21 :34-44 (2017).

Damino, et al., "Comparison of the capsular response to the Biocell RIV and Mentor 1600 Siltex breast implant surface texturing: a scanning electron microscopic study", Plast. Reconstr. Surg. 2001, 108(7), 2047-2052.

DeBruijn, et al, "Mastopexy with Mesh Reinforcement: The Mechanical Characteristics of Polyester Mesh in the Female Breast," Plast. Reconstr. Surg. 124: 364, 2009.

DeBruijn,et al, "Mastopexy with 3D Preshaped Mesh for Long Term Results: Development of the Internal Bra System," Aesth Plast Surg., 32:757-765, DOI 10.1007/s00266-008-9186-y, 2008.

European Search and Opinion dated Jul. 3, 2017, for 12754773.5-1666.

Goes, "Periareolar mammaplasty: double skin technique with application of polyglactine or mixed mesh," Plast. Reconstr. Surg.97-959-68 (1996).

Goes, "Periareolar mammaplasty: double-skin technique with application of mesh support," Clin Plastic Surg 29 (2002) 349-364.

(56) References Cited

OTHER PUBLICATIONS

Goes, "Periareolar Mastopexy with FortaPerm," Aesth. Plast. Surg., 34-350-8, 2010.
Gorbet et al. Biomaterials, 26:6811-6817 (2005).
ISR and Written Opinion for PCT/US2019/015849, dated Apr. 23, 2019.
Johnson, Gerald W., "Central core reduction mammoplasties and Marlex suspension of breast tissue," Aesthetic Plastic Surgery 5:77-84, 1981.
Leberfinger et al., "Breast-implant associated anaplastic large cell lymphoma: a systematic review", JAMA Surg. Dec. 1, 2017; 152(12), 1161-1168.
Malluci, Concepts in aesthetic breast dimensions: Analysis of the ideal breast, Journal of Plastic, Reconstructive & Aesthetic Surgery (2012) 65, p. 8-16.
Malluci, Design for Natural Breast Augmentation: The ICE Principle, Plastic and Reconstructive Surgery, Jun. 2016, vol. 137. No. 6, 1728-1737.
Malluci, Population Analysis of the Perfect Breast: A Morphometric Analysis, (2014), www.PRSJournal.com, vol. 134, No. 3 • The Perfect Breast, p. 436-447.
Maxwell and Gabriel, "The evolution of breast implants", Plast. Reconstr. Surg. 134:12S, 2014.
O'shaughnessy, "Evolution and update on current devices for prosthetic breast reconstruction", Gland Surgery, 2015, 4(2):97-110.
P. van Deventer, Improving the Longevity and Results of Mastopexy and Breast Reduction Procedures: Reconstructing an Internal Breast Support System with Biocompatible Mesh to Replace the Supporting Function of the Ligamentous Suspension, Aesth Plast Surg (2012) 36:578-589, DOI 10.1007/s00266-011-9845-2.
Ray, J.A. et al., "Polydioxanone (PDS), A Novel Monofilament Synthetic Absorbable Suture", Surgery, Gynecology & Obstetrics, Oct. 1981, vol. 153, 497-507.
Sieber et al., "Clinical evaluation of shaped gel breast implant rotation using high-resolution ultrasound", Aesthetic Surgery Journal, 2017, vol. 37 (3), 290-296.
Slavin, "The use of acellular dermal matrices in revisional breast reconstruction", Plast. Reconstr. Surg. 2012, 130 (Suppl. 2): 70S-85S.
Supplementary European Search Report of the EPO dated Jul. 30, 2014, EP 12754773.5 from PCT/US2012/027075.
Williams "Poly-4-hydroxputyrate (P4HB): a new generation of resorbable medical devices for tissue repair and regeneration," DOI 10.1515/bmt-2013-0009 Biomed Tech 2013; 58(5): 439-452.
Written Opinion of IPEA dated Jun. 15, 2015 for PCT/US2014/046420.
Written Opinion of ISR dated Nov. 5, 2012 for PCT/US2012/027975.
Hans de Bruijn, Siegmund Johannes, "Mastopexy with 3D Preshaped Mesh for Long Term Results: Development of the Internal Bra System," Aesth Plast Surg., 32:757-765, DOI 10.1007/s00266-008-9186-y, 2008.
PCT International Search Report and Written Opinion of the International Searching Authority, dated Nov. 5, 2012 application No. PCT/US2012/027975.
Supplementary European Search Report of the EPO dated Jul. 30, 2014 EP 12754773.5 from PCT/US2012/027975.
Written Opinion of the ISA, dated Apr. 13, 2021, for PCT/US2020/060809.
Nimboriboonporn et al., Nipple-areola complex reconstructions. Gland Surg. Feb. 3, 2014; 3(1):35-42.
U.S. Appl. No. 16/797,960, filed Feb. 21, 2020, Felix et al.
U.S. Appl. No. 16/950,064, filed Nov. 17, 2020, Limem et al.
U.S. Appl. No. 17/486,879, filed Sep. 27, 2021, Limem et al.
U.S. Appl. No. 17/486,886, filed Sep. 27, 2021, Limem et al.
U.S. Appl. No. 29/735,730, filed May 22, 2020, Limem et al.
U.S. Appl. No. 29/736,445, filed May 9, 2020, Limem et al.
U.S. Appl. No. 29/798,823, filed Jul. 10, 2021, Limem et al.
Extended European Search Report for European Application 19869949.8 dated May 31, 2022.
U.S. Appl. No. 17/871,155, filed Jul. 22, 2022, Felix et al.

\* cited by examiner

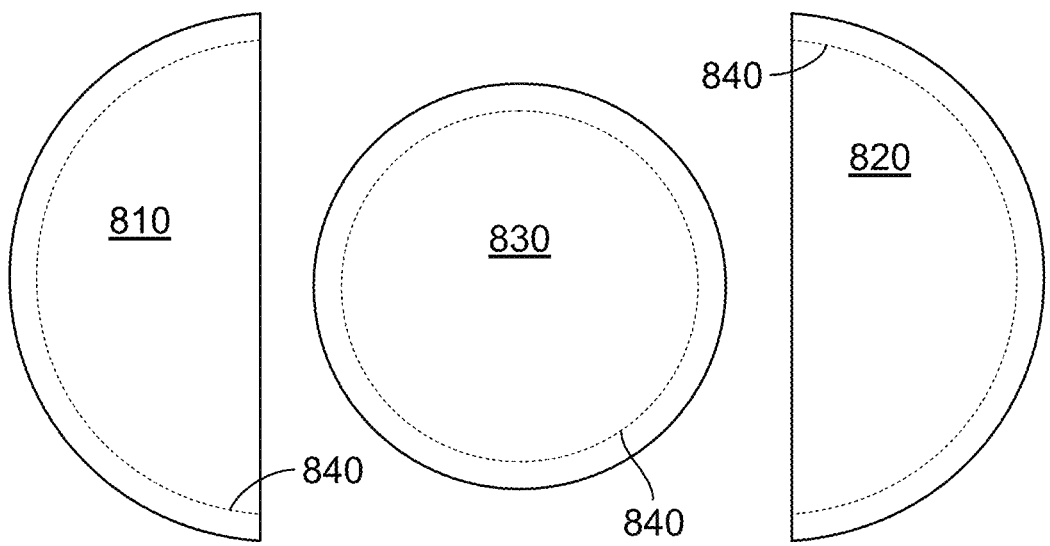
FIG. 15
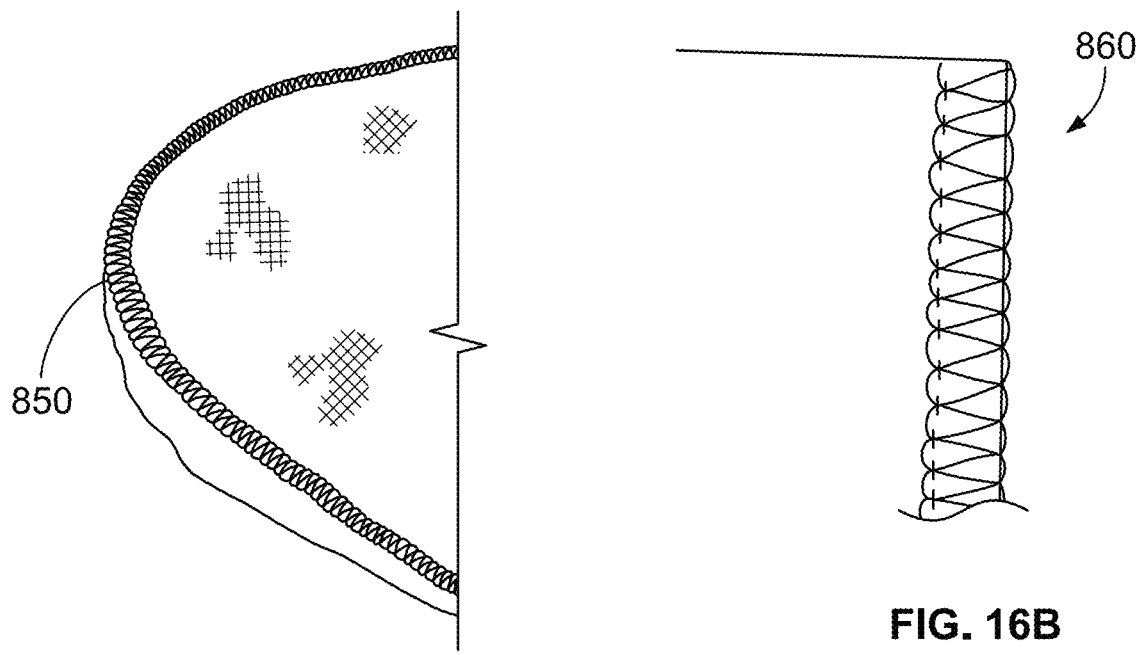
FIG. 16A
FIG. 16B

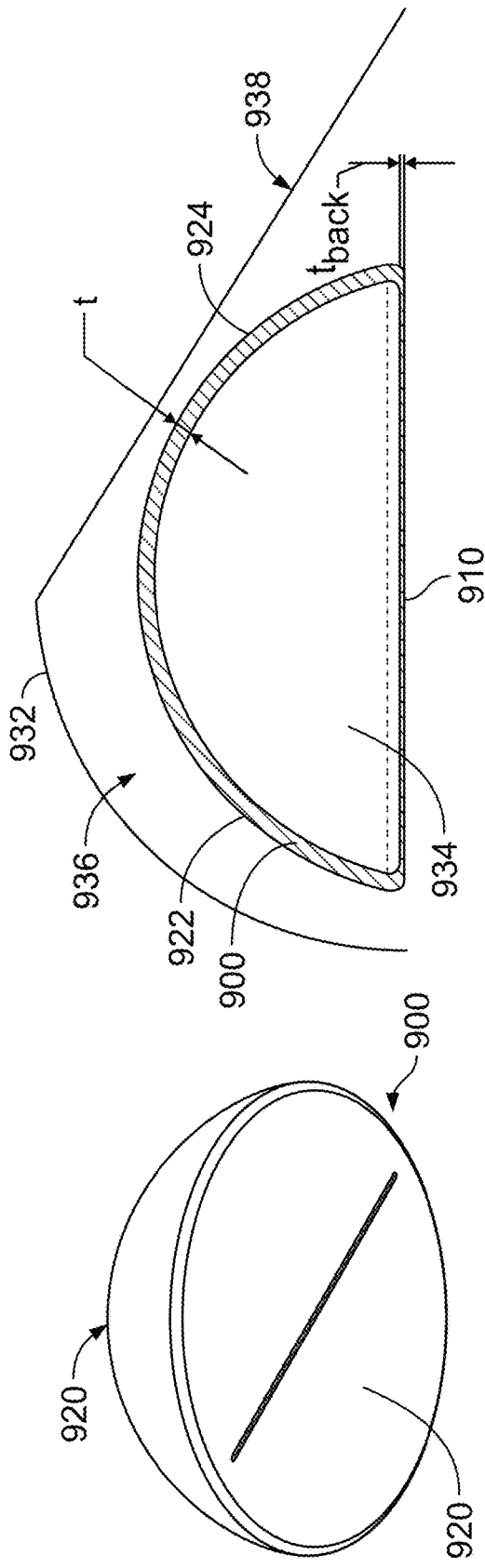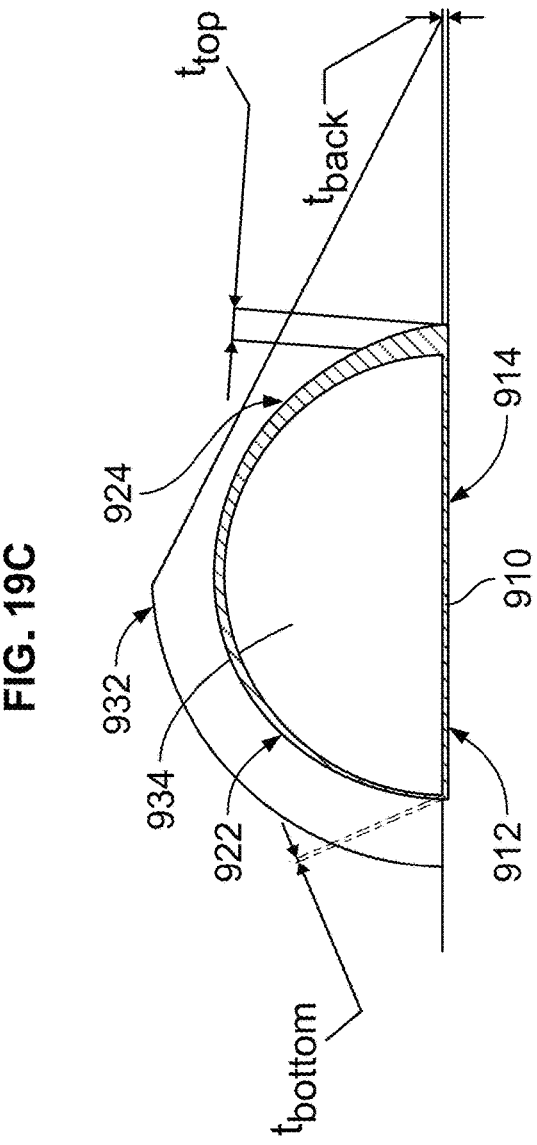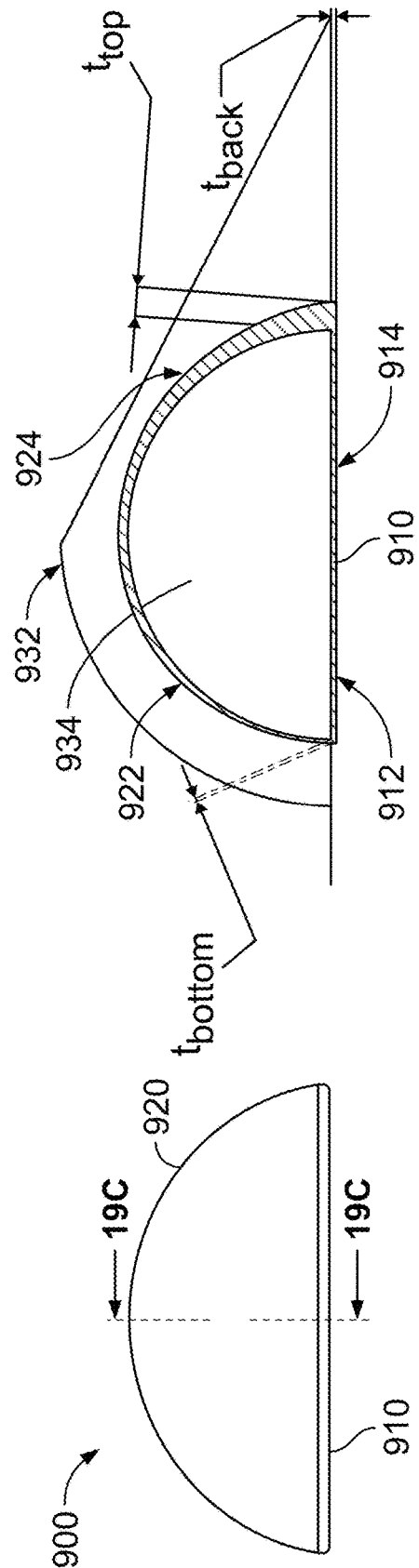

MEDICAL DEVICES TO LIMIT MOVEMENT OF BREAST IMPLANTS

CROSS REFERENCE TO RELATED APPLICATIONS

The present application claims priority to U.S. Ser. No. 62/740,146, filed Oct. 2, 2018, and U.S. Ser. No. 62/868,298, filed Jun. 28, 2019, each of which is incorporated in its entirety by reference for all purposes.

FIELD OF THE INVENTION

The present invention generally relates to the field of surgery, and more particularly, to implantable medical devices that limit the movement of breast implants following breast reconstruction, including augmentation mastopexy.

BACKGROUND OF THE INVENTION

Breast reconstruction following mastectomy has become an integral and important part of breast cancer treatment with the surgery providing the patient with both aesthetic and psychosocial benefits. Nearly 65% of US breast reconstruction procedures now use a tissue expander (TE) which is temporarily implanted in the breast to create a pocket for a permanent breast implant in the first step of the procedure. Tissue expanders are now more frequently placed on top of the chest muscle (pre-pectoral placement) rather than under the chest muscle in order to reduce post-operative pain. Once a pocket is created, the TE is removed and replaced with a permanent breast implant in a second step. In some patients, however, it is possible to form a pocket for the breast implant following mastectomy without the use of a TE.

Breast implants can also be used in breast augmentation and mastopexy procedures to augment breast size. In the latter procedure, a breast lift is combined with breast augmentation. Most commonly, the breast implant is placed in a pocket under the breast tissue, but in some cases, it is implanted under the chest wall.

Breast implants differ in dimensions, shape, and surface texture. A wide variety of different dimensions are available allowing the surgeon and patient to select from a range of projections, heights, widths and overall volume. In terms of shape, there are round and anatomically shaped implants, and the surfaces of the implants may be smooth, micro-textured or macro-textured. The Siltex 1600 micro-textured breast implant, for example, has a surface with small open-pores of 70-150 µm diameters and depths of 40-100 µm, while the Biocell RTV macro-textured breast implant has larger open pores of 600-800 µm diameter with depths of 150-200 µm (Damino et al. Comparison of the capsular response to the Biocell RTV and Mentor 1600 Siltex breast implant surface texturing: a scanning electron microscopic study, Plastic and Reconstructive Surgery, 2001, 108(7), 2047-2052).

Recent studies using high-resolution ultrasound, however, have discovered that macro-texturing is not sufficient to prevent breast implant rotation. Sieber et al. (Clinical evaluation of shaped gel breast implant rotation using high-resolution ultrasound, Aesthetic Surgery Journal, 2017, Vol 37 (3), 290-296) have reported that the implant rotation rate in patients implanted with anatomical breast implants manufactured by Mentor and Allergan was 27%. Furthermore, a staggering 26% of the implants checked had rotated 45° from the midline. Sieber et al. concluded that rotation of breast implants was occurring in 42% of patients.

Rotation of anatomic breast implants is clearly a major problem because the capsule that forms around the implant cannot latch onto the implant and hold it in place. No patient wants to find out that their anatomical implant has rotated, and that the thicker part of the implant is no longer located at the bottom of the breast, but instead is located to the side or even at the top of the breast. Particularly when the only way to resolve the problem is by further surgery.

Concern over the use of macro-textured anatomical breast implants is not limited to undesirable rotation of the implants resulting in a suboptimal appearance of the breasts. A growing body of evidence is associating the use of these implants with a serious rise in cases of anaplastic large cell lymphoma (ALCL), a rare peripheral T-cell lymphoma, that can be fatal (Leberfinger et al., Breast-implant associated anaplastic large cell lymphoma: a systematic review, JAMA Surg. 2017, Dec. 1; 152(12), 1161-1168). Chronic inflammation resulting from the macro-texturing of the anatomical breast implants is thought to be the underlying mechanism. The chronic inflammation is believed in certain cases to trigger a malignant transformation of T cells resulting in a cancer of the immune system. Treatment of the lymphoma involves removal of the patient's implant and the capsule surrounding the implant, and in more advanced cases, the patient may require further treatment including radiotherapy, chemotherapy, and lymph node dissection. On account of the rise in cases of breast implant-ALCL, the FDA has advised patients to discuss the risks associated with breast implants that have macro-textured surfaces, as well as smooth surfaces, and some surgeons are decreasing or discontinuing their use of macro-textured breast implants.

While rotation of smooth breast implants does not necessarily change the appearance of the breast, breast implant-ALCL with smooth breast implants has been reported albeit at a lower incidence rate than with patients implanted with macro-textured anatomical implants. Furthermore, it has been reported that the rate of capsular contraction, which results from a thickening of the thin flexible capsule that initially surrounds the implant, is higher for smooth implants than for anatomical implants (Damino, et al., Comparison of the capsular response to the Biocell RTV and Mentor 1600 Siltex breast implant surface texturing: a scanning electron microscopic study, Plast. Reconstr. Surg. 2001, 108(7), 2047-2052). While the reason for the greater rate of capsule contraction is not fully understood, it has been postulated that the higher rate of capsule contraction results from a higher rate of rotation and more movement of the smooth round breast implants. Capsular contraction can be a serious problem, and is relatively common. It can occur soon after implantation or 20-30 years later. Contraction of the capsule that forms around the implant can cause chronic pain, and a feeling of tightness around the breast. This can be treated either by capsulotomy where the implant is removed, incisions are made in the capsule, and the implant is replaced. Or, contraction of the capsule can be treated by capsulectomy where both the implant and the capsule are removed, and a new implant is implanted in the patient. Avoiding the need to perform these procedures would be preferable.

In addition to the problems associated with the rotation of breast implants, movement of either type of breast implant is undesirable because it will produce an unnatural appearance of the breast. Despite movement of breast implants being undesirable, it is still not unusual. In one study of 715 reconstruction patients, 71.5% of patients at 10 years had undergone reoperation for implant malposition (O'Shaughnessy, 2015, Evolution and update on current devices for prosthetic breast reconstruction, Gland Surgery, 4(2):97-110). Displacements of an implant can occur if the shape of the pocket for the implant is not precise, and physical activity can also result in implant displacement. Movement of an implant can also occur if supporting tissues around the implant stretch or become thinner, or if there is a loss of elasticity of the tissues. These conditions can, for example, result in "bottoming out" where the implant moves lower resulting in an unattractive appearance (see, Slavin, 2012, The use of acellular dermal matrices in revisional breast reconstruction, Plast. Reconstr. Surg. 130 (Suppl. 2): 70S-85S). These conditions can also result in the implant pocket stretching laterally causing the patient's breast implants to move sideways towards their sides or arm pits, particularly when lying down.

Various implantable devices have been developed to create pockets for breast implants or for use as slings in breast reconstruction. Acelluar dermal matrix (ADM), for example, has been used to cover tissue expanders (Bertozzi, N. *Ann Med Surg.* 21:34-44 (2017)). In a typical procedure, the pectoralis major muscle is mobilized, and the ADM is attached to the edge of the muscle in order to create a sling and submuscular pocket for the tissue expander. The use of ADM eliminates the need to release and elevate the serratus anterior muscle, the pectoralis minor muscle, and the rectus abdominis fascia, and consequently reduces postoperative pain. Such devices, however, are not designed to limit rotation of breast implants.

U.S. Pat. No. 4,936,858 to O'Keeffe also discloses pouches for breast implants, made from non-biodegradable yarn. The diameters of the pouches exceed that of the implant by approximately 20%. The pouches are not designed to limit rotation of the breast implants.

U.S. Pat. No. 7,520,896 to Benslimane shows a breast implant with a support element (5) attached to the breast implant using adhesive (4), and a securing element (3) connected to the support element. The support element (5) can be attached to the patient's pectoral muscle or in the area of the axilla. FIG. 5 of Benslimane shows a breast implant that comprises two packages, an outer package and an inner package designed to prevent contamination of the breast implant by microbes. The outer package is non-sterile. The pouch, however, is not designed to limit rotation or migration of any breast implant, and is not designed for implantation since the outer package is non-sterile.

U.S. Patent Application No. 20070196421 to Hunter discloses sleeves for breast implants that comprise fibrosis-inhibiting drugs, but does not disclose sleeves that are designed to limit rotation of breast implants.

U.S. Patent Application No. 20080128315 to Buevich discloses resorbable pouches for implantable medical devices, but does not disclose pouches for breast implants, or pouches designed to limit rotation of breast implants.

U.S. Patent Application No. 20020165596 to Wilson discloses resorbable pouches for placement of bone graft or bone graft substitutes, but does not discloses pouches for breast implants, or pouches designed to limit rotation of breast implants.

U.S. Pat. No. 5,383,929 to Ledergerber discloses coverings for implants that disorganize scar tissue at the implant/body interface. The coverings are preferably made from expanded PTFE, a non-degradable polymer.

WO2019/094861 to Mlodinow discloses mesh pouches for securing implants within a patient's body. The mesh pouches may be used to support a breast implant.

Notwithstanding the above, there is still a need for devices as described herein that can limit not only rotation of breast implants, but also the movement of breast implants. There is also a need for new breast implants that have been designed specifically for use with medical devices that limit their ability to rotate in vivo. There is yet another need to develop breast implant fixation devices that not only limit movement of breast implants, but prevent the breast implant from being palpable, or that hide any ripples or indentations in the breast resulting from implantation of breast implants.

SUMMARY OF THE INVENTION

Medical devices are described herein that limit the movement of breast implants. In embodiments, pouches anchor in place in tissues at the site of implantation, and will not migrate or rotate. Breast implants may be incorporated or inserted into the pouches, preferably prior to implantation, limiting their ability to rotate or migrate. The pouches may also prevent the breast implants from being palpable, or prevent the formation of ripples or indentations on the skin following placement of the breast implants. The pouches limit rotation and migration of the breast implants by applying compressive forces on the breast implants, allowing tissue in-growth into the pouches, or interlocking with the breast implants, or combinations thereof. The interlocking mechanism provides a physical barrier to the rotation or migration of the breast implants when inserted in the pouches. The breast implants may be fully or partially encased by the pouches. The pouches eliminate the problem of palpability or formation of skin indentations and ripples by providing a thick layer on the front of the pouch that sits between the patient's skin and the breast implant.

New breast implants for use with the pouches are also described. The new breast implants have features that are designed to interlock with the medical devices so that rotation or migration of the breast implants is limited when implanted with the pouches. The interlocking mechanism provides a physical barrier to the rotation or migration of the new breast implants when inserted in the pouches. In embodiments, a fixation means mechanically secures the breast implant to the pouch. The new breast implants may comprise tabs or other features that interlock with the pouches to prevent rotation. Interlocking provides a physical barrier to limit rotation or migration of the new breast implants.

Methods to prepare the pouches and new breast implants are also described. The pouches are preferably made with absorbable polymers, most preferably with poly-4-hydroxybutyrate (P4HB) and copolymers thereof, or poly(butylene succinate) or copolymers thereof. The pouches are preferably prepared with porosity that allows tissue in-growth, and anchoring of the pouches at the site of implantation. Preferably, the pouches are prepared with fibers, and most preferably with monofilament fibers or dry spun fibers. Preferred methods of manufacturing the pouches include thermoforming, knitting, and dry spinning.

Also disclosed are methods of using the pouches with breast implants in breast reconstruction, and breast augmentation, including augmentation mastopexy. The breast implants may be filled with either silicone or saline. The pouches may be used following mastectomy in either one-stage or two-stage breast reconstruction procedures. In the latter case, a preferred method involves mobilizing the pectoralis major muscle, creating a submuscular pocket for a tissue expander (TE), optionally by attaching an acellular dermal matrix, P4HB textile or textile comprising polybutylene succinate or copolymer thereof to the elevated pectoralis major muscle, inflating the TE, removing the TE, and implanting the pouch containing a breast implant in the submuscular pocket.

In breast augmentation procedures, the pouch containing a breast implant may be placed in a breast pocket created either in the subglandular position (above the pectoral muscle) or in the submuscular position (below the pectoral muscle). When used in breast augmentation, the pouch and breast implant may be inserted using transaxillary or transumbilical methods, or following a peri-areolar incision or incision at the inframammary fold (IMF).

A pouch for a breast implant to hold and prevent rotation of the breast implant in a patient comprises a front sheet and a back sheet joined to the front sheet along a medial edge and a lateral edge. Each of the front sheet and back sheet are made of a material comprising a plurality of pores for tissue ingrowth. The pouch further comprises at least one seam spanning the medial edge to the lateral edge thereby forming a cavity wherein the size and shape of the cavity is adapted to enclose the breast implant. The seam has a curvature and is located relative to the medial edge and the lateral edge to create an increased tension force on the breast implant in the vicinity of the seam serving to firmly hold and prevent rotation of the breast implant within the cavity.

In embodiments, the seam is located in the lower region of the pouch and comprises a concave curvature.

In embodiments, the pouch further comprises a second seam in the upper region and the second seam has a convex curvature.

In embodiments, the first seam and the second seam are formed by knitting or welding.

In embodiments, the pouch further comprises a slit on the back sheet to provide access to the cavity for the breast implant.

In embodiments, the pouch is formed of an elastic material and the cavity is undersized relative to the breast implant such that the cavity is elastically expanded when the breast implant is inserted therein.

In embodiments, the pouch comprises an auxetic structure, and in a particular embodiment is an auxetic mesh.

In embodiments, the pouch further comprises a non-woven coating on the front sheet where the NAC is to contact.

In embodiments, the pouch comprises a first substantially planar 2D configuration, and a second 3D configuration when the breast implant is disposed in the cavity.

In embodiments, the back sheet comprises a smooth alignment protrusion adapted to atraumatically and locally deform the breast implant thereby prohibiting the breast implant from rotating relative to the pouch in situ. The smooth alignment protrusion may be made of (or comprise) the same material that the sheets are made from.

In embodiments, the pouch further comprises a mesh extension region extending outwardly from the at least one seam. The mesh extension region may comprise a plurality of discrete tabs.

In another embodiment, a pouch of a breast implant fixation device comprises a back for placement on the chest wall of the patient, a front bottom for placement in the lower pole of the breast, a front top for placement in the upper pole of the breast, and a front intermediate region between the front top and the front bottom for placement under the skin of the patient; and is porous in order to allow tissue in-growth and limit movement of the breast implant.

In embodiments, the pouch comprises a slit or opening on the back to allow insertion of the breast implant into the pouch.

In embodiments, the front of the pouch of the breast implant fixation device is thicker than the back of the pouch.

In embodiments, the elasticity of the front of the pouch of the breast implant fixation device is higher than the elasticity of the back of the pouch. The elasticity of the pouch makes is easy to insert the breast implant in the pouch, and provides a tight conformation around the breast implant.

In embodiments, one of the mechanical properties selected from the group consisting of porosity, thickness, and elasticity vary along the front area of the pouch from the top to the bottom. In a particular embodiment, the thickness decreases in the front of the pouch from the top to the bottom.

In embodiments, the porosity of the pouch is adjusted to facilitate wrapping the breast implant in the pouch, particularly when the breast implant is round. Varying the pore sizes in different regions of the pouch provides the pouch with different properties in the corresponding regions (namely, the front, back, bottom and top of the pouch). In embodiments, a device includes larger pores in the back of the pouch to provide a less dense pouch that is more drapable.

In embodiments, a device includes smaller pores in the front of the pouch to increase the surface area of the front of the pouch relative to the back of the pouch, and to increase the surface area that is able to hold fat. In embodiments, fat is applied to the front of the pouch, and in a particular embodiment, autologous fat is applied or otherwise provided on the front of the pouch prior to implantation.

In embodiments, a flexible breast implant fixation device to prevent migration of the breast implant comprises a pouch shaped to cover the breast implant wherein the pouch is adapted to engage the breast implant preventing the breast implant from substantially rotating inside the pouch; and wherein the pouch further comprises a plurality of outwardly extending (or protruding) anchors, and wherein the anchors are characterized by fibrous or filament-type construction, and optionally, wherein the density of the anchors ranges from 10-50 anchors per square cm, and optionally, 20-30 anchors per square cm.

In view of the foregoing, it is thus an object of the invention to provide medical devices, e.g., pouches, for use with breast implants that limit movement, including rotation or migration, of the breast implants.

It is another object of the invention to provide new breast implants with features that limit their movement in vivo, including rotation, when used with the pouches.

It is still another object of the invention to provide breast implant fixation devices that not only limit migration of breast implants, but prevent the breast implant from being palpable, or that prevent the formation of any ripples or indentations when breast implants are placed in the breasts.

It is yet another object of the invention to provide methods to prepare or manufacture pouches that limit movement of breast implants, and methods to prepare new breast implants with features that limit their movement in vivo.

It is still another object of the invention to provide methods to implant the pouches and breast implants.

These and other objects, aspects, and advantages of the subject invention shall become apparent in view of the following description with reference to the accompanying figures.

BRIEF DESCRIPTION OF THE DRAWINGS

FIG. 15 is a diagram showing a process to construct a breast implant fixation pouch from two semicircular meshes and a round mesh by sewing the pieces together along the indicated stitch lines in accordance with an embodiment of the invention.

FIG. 16A depicts the stitched edge of a breast implant fixation pouch constructed as shown in FIG. 15.

FIG. 16B is a diagram showing the stitch pattern used to stitch the edge of the breast implant fixation pouch constructed in FIG. 16A.

FIGS. 19A, 19B are back perspective and side views, respectively, of a pouch for holding an implant in accordance with an embodiment of the invention.

FIG. 19C is a cross sectional view of the pouch shown in FIG. 19B taken along line 19C-19C in situ, and illustrating the front of the pouch having a greater thickness than the back of the pouch.

FIG. 20 is a cross sectional view of another pouch in situ for holding an implant illustrating the front of the pouch having a thickness that varies from the top of the pouch to the bottom of the pouch in accordance with an embodiment of the invention.

DETAILED DESCRIPTION OF THE INVENTION

Figure 1:
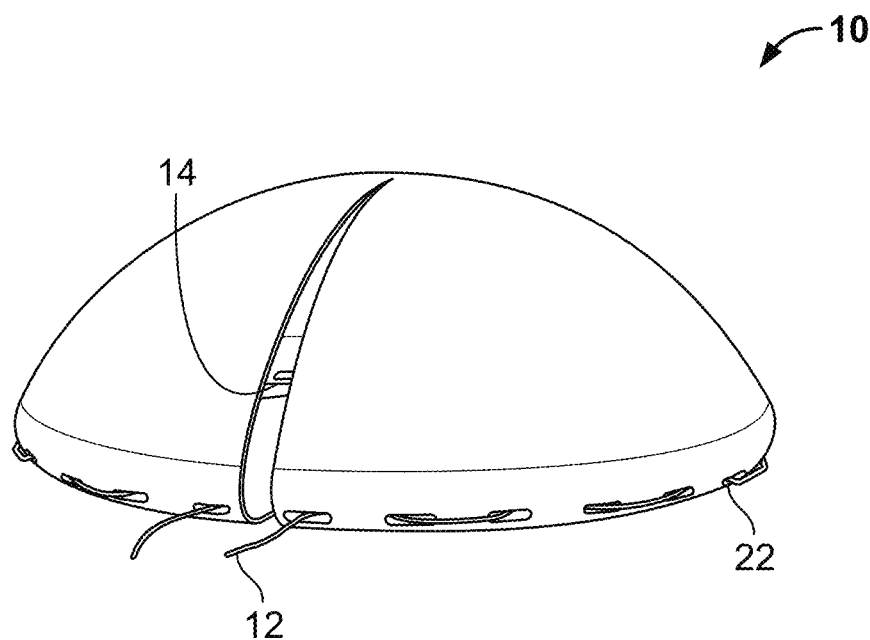
FIG. 1 is an isometric view of an implantable pouch in accordance with an embodiment of the invention including a slit for insertion of a breast implant and a tightenable draw cord serving to apply pressure on the breast implant and limit its rotation or migration after implantation.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

In embodiments of the invention, an implantable medical device for the surgeon limits rotation or migration of a breast implant, maintains the patient's physical appearance, and decreases the chances of capsular contraction and the development of breast-implant associated lymphoma. The medical device used to prevent migration and rotation of a breast implant can be made for use with a wide variety of types of breast implants, and used in breast reconstruction procedures following mastectomy as well as breast augmentation procedures, including augmentation mastopexy procedures.

In embodiments, the medical device is a pouch, and is utilized by inserting the breast implant inside the pouch and securing the breast implant inside the pouch so it is unable to rotate inside the pouch. Preferably, the breast implant cannot rotate more than 45 degrees inside the pouch, and more preferably the breast implant cannot rotate more than 30 degrees inside the pouch. After securing the breast implant inside the pouch, the pouch containing the breast implant is then implanted in the breast by the surgeon. Rotation and migration of the breast implant is prevented after implantation by tissue growth into the pouch which anchors the pouch and therefore the breast implant in place. Preferably, the pouch is made from synthetic polymeric material to reduce the risk of disease transmission associated with human or animal-derived implants.

In embodiments, the medical device is a breast implant fixation device comprising a pouch, and is utilized by inserting the breast implant in the pouch. The pouch is porous and allows tissue in-growth. Tissue in-growth fixates the pouch in place and prevents migration of the breast implant. Palpability of the breast implant is reduced or eliminated by the enhanced or optimized thickness of the front of the pouch which separates the patient's skin and the breast implant. The enhanced or optimized thickness of the front of the pouch also reduces or eliminates the appearance of indentations or ripples on the patient's skin due to the presence of the breast implant.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body.

"Average pore size diameter" as used herein is calculated using open source ImageJ software available at https://imagej.nih.gov/ij/index.html.

"Bioactive agent" is used herein to refer to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Breast implant" as used herein refers to a prosthesis that is implanted in place of a female breast, but can also be implanted to change the size, shape and contour of a woman's breast.

"Burst strength" as used herein is determined by test method ASTM D6797-02 "Standard test method for bursting strength of fabrics constant rate of extension (CRE) ball burst test," using a MTS Q-Test Elite universal testing machine or similar device. The testing fixture uses a ⅜ inch diameter ball.

"Copolymers of poly(butylene succinate)" as generally used herein means any polymer containing 1,4-butanediol units and succinic acid units with one or more different diols, diacid or hydroxycarboxylic acid units, including hydroxycarboxylic acid groups with one or more carboxylic acid or hydroxy acid groups. The copolymers may also comprise chain extenders, coupling agents, cross-linking agents or branching agents.

"Copolymers of poly-4-hydroxybutyrate" as generally used herein means any polymer containing 4-hydroxybutyrate with one or more different hydroxy acid units.

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Inframammary fold" or "IMF" as generally used herein is the position where the lower pole of the breast meets the chest wall.

"Lower pole" as generally used herein means the part of the breast located between the inframammary fold (IMF) and the nipple meridian reference, and protruding away from the chest wall.

"Macro-porous" materials or structures as used herein have average pore size diameters of at least 25 microns, more preferably at least 50 microns, and even more preferably at least 75 microns.

"Molecular weight" as used herein, unless otherwise specified, refers to the weight average molecular weight (Mw), not the number average molecular weight (Mn), and is measured by GPC relative to polystyrene.

"Nipple meridian reference" or "NMR" is the plane drawn horizontally through the nipple to the chest wall.

"Oriented" as generally used herein refers to molecular alignment of polymer chains in a material. A polymer that has been stretched becomes partly oriented and then highly oriented, and the tensile strength increases with increasing orientation. For example, an unoriented polymeric fiber may be stretched to orient the fiber which results in a polymeric fiber with higher tensile strength. An "oriented mesh" means a mesh made with oriented fibers.

"Poly-4-hydroxybutyrate" as generally used herein means a homopolymer containing 4-hydroxybutyrate units. It can be referred to herein as Tepha's P4HB™ polymer or Tepha-FLEX® biomaterial (manufactured by Tepha, Inc., Lexington, Mass.).

"Poly(butylene succinate)" as generally used herein means a polymer containing 1,4-butanediol units and succinic acid units.

"Strength retention" as used herein means the amount of time that a material maintains a particular mechanical property following implantation or exposure to a particular set of conditions. For example, if the stress required to break a multifilament yarn or monofilament fiber after one month is half of its original value then the multifilament or monofilament fiber is said to have a 50% strength retention after one month.

"Suture pullout strength" as used herein means the peak load (kg) at which a breast implant fixation device fails to retain a suture. It is determined using a tensile testing machine by securing the breast implant fixation device in a horizontal plate, threading a suture in a loop through the breast implant fixation device at a distance of 1 cm from the edge of the breast implant fixation device, and securing the suture arms in a fiber grip positioned above the breast implant fixation device. Testing is performed at a crosshead rate of 100 mm/min, and the peak load (kg) is recorded. The suture is selected so that the breast implant fixation device will fail before the suture fails. The suture pullout strength may be converted and expressed as Newtons.

"Tensile modulus" is the ratio of stress to strain for a given material within its proportional limit.

"Tissue expander" ("TE") as used herein means a breast implant that is placed temporarily in the breast to expand tissues and make room for a breast implant. The TE is expanded (e.g., inflated) periodically, for example, by injecting a liquid or gas into the TE. The TE is removed once the tissue has been sufficiently stretched to make room for a permanent breast implant.

"Upper pole" as generally used herein means the top part of the breast located between the nipple meridian reference and the position at the top of the breast where the breast takes off from the chest wall, and protruding away from the chest wall.

II. Materials for Preparing Pouches to Limit Movement of Breast Implants

In accordance with embodiments of the invention described herein, implantable medical devices limit the movement of breast implants. In particular embodiments, the medical devices are in the form of a pouch sized to enclose the breast implant. In embodiments, the pouches are porous, and fixated in place by tissue in-growth. The pouches anchor at the site of implantation, and in embodiments limit movement of the breast implants by applying compressive or frictional forces to the breast implants, or interlocking with the breast implants. In embodiments, the pouches prevent the breast implants from rotating inside the pouches. In embodiments, the pouches anchor at the site of implantation, and prevent pocket stretch, lateral displacement of the implant, and ptosis by preventing or limiting migration of the breast implant.

With reference to FIGS. 19A-19C, an embodiment of a pouch 900 in accordance with the subject invention is shown. As described further herein, the pouch 900 is preferably porous and has a back 910 for placement on the chest wall of the patient, and a front 920 for placement under the skin 932 of the patient. In embodiments, the front 920 of the pouch has a thickness (t) sufficient to hide any ripples or indentations in the patient's skin when a breast implant 934 is placed in the pouch, and the pouch is placed in the patient's breast. The thickness (t) of the pouch is also preferably sufficient to prevent the breast implant from being palpable. An exemplary range for the thickness (t) on the front face is 0.5-10 mm and more preferably from 0.5-3 mm, or 0.75-3 mm. In embodiments, the front of the pouch has a thickness to prevent palpability and the appearance of ripples or indentations on the patient's skin. In the embodiment shown in FIG. 19C, the thickness (t) of the front 920 of the pouch is uniform from the top 924 to the bottom 922. Additionally, the front 920 of the pouch can be thicker than the back 910 of the pouch. The thickness of the front 920 may be a factor of 2 to 5 times greater than the thickness of the back of the pouch. In embodiments, the thickness of the back of pouch ranges from 0.2-0.4 mm.

However, in other embodiments, the thickness of the pouch or other mechanical properties described herein vary along the front of the pouch from the top 924 to the bottom 922, or otherwise. In the embodiment shown in FIG. 20, for example, the thickness decreases along the pouch from the top to the bottom. The front top 924 ($t_{top}$) may have a thickness of 5-10 times greater than the front bottom 922 ($t_{bottom}$). Additionally, in a preferred embodiment, the back 910 has a thickness less than the front.

The elasticity may also vary along the regions of the pouch. In embodiments, a pouch has a back 910 for placement on the chest wall of the patient, and a front 920 for placement under the skin 932 of the patient, and an elasticity of the front area 932 of the pouch of 15-75%, and more preferably 30-65%, and an elasticity of the back area 910 of the pouch of 5-25%, and more preferably 8-20%, when the elasticities are measured as the percent increases of the areas when the areas are subject to deformation in ASTM burst method D6797-02 using a round ball. In a particularly preferred embodiment, the elasticity of the front area is 30-65%, and the elasticity of the back area is 5-25%. The elasticities of the front and back areas allow the breast implant 934 to be easily inserted in the pouch with the pouch conforming tightly to the contours of the breast implant.

In embodiments, the pouches for the breast implants have different porosities in different regions 910, 920 of the pouch, or different amongst front regions 922, 924 and an intermediate spanning from the front bottom region 922 to front top region 924.

In embodiments, with reference to FIG. 19C, a pouch has large average pore size diameters on the back 910 of the pouch and around the perimeter of the pouch to improve the drapability of the breast implant, and smaller average pore size diameters on the front top 924 of the pouch (which is placed in the front upper pole 938 of the breast) to increase the surface area available for holding fat graft. In embodiments, the front superior area 924 of the pouch is more dense than the back of the pouch.

In embodiments, the fixation devices prohibit rotation of the enveloped breast implant by more than 45 degrees, and more preferably by more than 30 degrees. In embodiments, the pouches prevent migration of the breast implants by more than 5 cm. The pouches partially or completely cover the breast implants. Preferably the breast implants are inserted inside the pouches prior to implantation. The pouches are preferably porous, and allow tissue in-growth. The dimensions of the pouches are tailored to accommodate the size and shape of the breast implant being implanted. The dimensions of the breast implants are selected by the surgeon according to the needs of the patient, and the patient's preferences.

The pouches are preferably made of absorbable polymers. Additionally, the pouches may be made from a single component, such as an unoriented, partially or fully oriented monofilament fiber or fibers, including non-wovens and knitted mesh, or from two or more components, such as fibers, textiles or films with different properties. The pouches can optionally comprise bioactive agents, as well as cells, including stem cells. The pouches so formed preferably have a pyrogen level of less than 20 endotoxin units per device, and can be sterilized.

A. Polymers for Preparing Pouches

The pouches may comprise degradable materials, and more preferably are made completely from degradable materials. In a preferred embodiment, the devices for fixation of breast implants are made from one or more absorbable polymers, preferably absorbable thermoplastic polymers and copolymers. The implantable pouch may, for example, be prepared from polymers including, but not limited to, polymers of glycolic acid, lactic acid, 1,4-dioxanone, trimethylene carbonate, 3-hydroxybutyric acid, 4-hydroxybutyrate, ε-caprolactone, 1,4-butanediol, and succinic acid, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates (PHA's); synthetically or biologically prepared polyesters; polycarbonates; tyrosine polycarbonates; polyamides (including synthetic and natural polyam ides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolactone and copolymers thereof, including random copolymers and block copolymers thereof. Preferably the absorbable polymer or copolymer will be substantially or completely resorbed two years after implantation.

Blends of polymers, preferably absorbable polymers, can also be used to prepare the pouches. Particularly preferred blends of absorbable polymers include, but are not limited to, polymers of glycolic acid, lactic acid, 1,4-dioxanone, trimethylene carbonate, 3-hydroxybutyric acid, 4-hydroxybutyric acid, ε-caprolactone, 1,4-butanediol, succinic acid or copolymers thereof.

In a particularly preferred embodiment, the pouches comprise poly-4-hydroxybutyrate (Tepha's P4HB™ polymer, Lexington, Mass.) or a copolymer thereof, and may in one embodiment be made completely with P4HB or copolymer thereof. Copolymers include P4HB with another hydroxyacid, such as 3-hydroxybutyrate, and P4HB with glycolic acid or lactic acid monomer. P4HB is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for processing and mechanical properties.

In another preferred embodiment, the pouches comprise a polymer comprising at least a diol and a diacid. In a particularly preferred embodiment, the polymer used to prepare the pouch is poly(butylene succinate) (PBS) wherein the diol is 1,4-butanediol and the diacid is succinic acid. The poly(butylene succinate) polymer may be a copolymer with other diols, other diacids or a combination thereof. For example, the polymer may be a poly(butylene succinate) copolymer that further comprises one or more of the following: 1,3-propanediol, 2,3-butanediol, ethylene glycol, 1,5-pentanediol, glutaric acid, adipic acid, terephthalic acid, malonic acid, methylsuccinic acid, dimethylsuccinic acid, and oxalic acid. Examples of preferred copolymers are: poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The poly(butylene succinate) polymer or copolymer may also further comprise one or more of the following: chain extender, coupling agent, cross-linking agent and branching agent. For example, poly(butylene succinate) or copolymer thereof may be branched, chain extended, or cross-linked by adding one or more of the following agents: malic acid, trimethylol propane, trimesic acid, citric acid, glycerol propoxylate, and tartaric acid. Particularly preferred agents for branching, chain extension, or crosslinking the poly(butylene succinate) polymer or copolymer thereof are hydroxycarboxylic acid units. Preferably the hydroxycarboxylic acid unit has two carboxylic groups and one hydroxyl group, two hydroxyl groups and one carboxyl group, three carboxyl groups and one hydroxyl group, or two hydroxyl groups and two carboxyl groups. In one preferred embodiment, the pouch comprises poly(butylene succinate) comprising malic acid as a branching, chain extending, or cross-linking agent. This polymer may be referred to as poly(butylene succinate) cross-linked or chain-extended with malic acid, succinic acid-1,4-butanediol-malic acid copolyester, or poly(1,4-butylene glycol-co-succinic acid), cross-linked or chain-extended with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly(butylene succinate)-malic acid copolymer refers to a copolymer prepared from succinic acid, 1,4-butanediol and malic acid. In another preferred embodiment, malic acid may be used as a branching, chain-extending or cross-linking agent to prepare a copolymer of poly(butylene succinate) with adipate, which may be referred to as poly[(butylene succinate)-co-adipate] cross-linked or chain-extended with malic acid. As used herein, "poly(butylene succinate) and copolymers" includes polymers and copolymers prepared with one or more of the following: chain extenders, coupling agents, cross-linking agents and branching agents. In a particularly preferred embodiment, the poly(butylene succinate) and copolymers thereof contain at least 70%, more preferably 80%, and even more preferably 90% by weight of succinic acid and 1,4-butanediol units. The polymers comprising diacid and diols, including poly(butylene succinate) and copolymers thereof and others described herein, preferably have a weight average molecular weight (Mw) of 10,000 to 400,000, more preferably 50,000 to 300,000 and even more preferably 100,000 to 200,000 based on gel permeation chromatography (GPC) relative to polystyrene standards. In a particularly preferred embodiment, the polymers and copolymers have a weight average molecular weight of 50,000 to 300,000, and more preferably 75,000 to 300,000. In one preferred embodiment, the poly(butylene succinate) or copolymer thereof used to make the pouch, or a component of the pouch, has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

B. Additives

Certain additives may be incorporated into the pouches, preferably in the absorbable polymer, copolymer or blends thereof that are used to make the pouch. Preferably, these additives are incorporated during a compounding process to produce pellets that can be subsequently melt-processed. For example, pellets may be extruded into fibers suitable for making the pouches. In another embodiment, the additives may be incorporated using a solution-based process, for example, fibers may be spun from solutions of the polymer and one or more additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the pouch, and to improve the mechanical properties of the pouch. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the pouches include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents

The pouches can be loaded or coated with bioactive agents. Bioactive agents may be included in the pouches for a variety of reasons. For example, bioactive agents may be included in order to improve tissue in-growth into the pouch, to improve tissue maturation, to provide for the delivery of an active agent, to improve wettability of the implant, to prevent infection, and to improve cell attachment.

The pouches may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The pouches can incorporate wetting agents designed to improve the wettability of the surfaces of the pouch to allow fluids to be easily adsorbed onto the pouch surfaces, and to promote cell attachment and or modify the water contact angle of the pouch surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The pouches can contain gels, hydrogels or living hydrogel hybrids to further improve wetting properties and to promote cellular growth throughout the thickness of the scaffold. Hydrogel hybrids consist of living cells encapsulated in a biocompatible hydrogel like gelatin, silk gels, and hyaluronic acid (HA) gels.

The pouches can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the pouches include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

The pouches may also comprise allograft material and xenograft materials, including acellular dermal matrix material and small intestinal submucosa (SIS).

In yet another preferred embodiment, the pouches may incorporate systems for the controlled release of the therapeutic or prophylactic agents.

D. Fibers

The pouches may comprise fibers. The fibers are preferably made from degradable thermoplastic polymers, and even more preferably from degradable thermoplastic polyesters. The fibers are preferably made from the degradable materials listed in section II.A above. In a preferred embodiment, the fibers are made from P4HB or copolymer thereof. In another preferred embodiment, the fibers are made from poly(butylene succinate) or copolymer thereof. The fibers maybe monofilament fibers, multifilament fibers, or combinations thereof. The fibers may be a yarn that is twisted, not twisted, or substantially parallel strands. The fibers may be unoriented, partially oriented, highly oriented or combinations thereof. Preferably, the fibers are highly oriented. The fibers may have elongation to break values of 3% to 1,100%, and more preferably from 10% to 100%. The fibers may have diameters ranging from 1 μm to 5 mm, more preferably from 10 μm to 1 mm, and even more preferably from 20 μm to 750 μm. The fibers in the pouch may have different weight average molecular weights. Preferably the polymers of the fibers have weight average molecular weights of 10 kDa to 1,200 kDa, but more preferably 50 kDa to 600 kDa. The fibers in the pouch may have different tensile strengths. Preferably, the tensile strength of the fibers in the pouch is 300-1,300 MPa. The fibers in the pouch are preferably flexible. Preferably, the fibers in the pouch have a tensile modulus of 70-1,000 MPa, and more preferably 400-1,000 MPa. The fibers may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The fibers of the pouch may have different degradation rates in vivo. Some fibers may degrade quickly while other fibers may degrade slowly. In another embodiment, the fibers comprise an additive or bioactive agent. The fibers can be produced by any suitable method but melt extrusion or solvent spinning are preferred.

In a preferred embodiment, the fiber is made from P4HB monofilament fiber. Suitable P4HB monofilament filament fibers can be produced by melt extrusion using the following method. Bulk P4HB resin in pellet form is dried to less than 300 ppm water using a rotary vane vacuum pump system. The dried resin is transferred to an extruder feed hopper with nitrogen purge to keep the pellets dry. The pellets are gravity fed into a chilled feeder section and introduced into the extruder barrel, which is 1.50 inches (3.81 cm) in diameter and fitted with an extrusion screw with a 30:1 L/D ratio. The extruder barrel contains 5 heating zones (or extrusion zones)—zones 1, 2, 3, 4 and 5. A suitable extruder is manufactured by American Kuhne. The heated and softened resin from the extruder is fed into a heated metering pump (melt pump) and from the melt pump the extruded resin is fed into the heated block and an eight-hole spinneret assembly. Processing profile ranges from 40° C. to 260° C. for temperatures, and 400 psi to 2000 psi for pressures, are used. The molten filaments are water quenched and conveyed into a three-stage orientation, with inline relaxation, before winding of the monofilaments on spools. Typical test values for extruded monofilament fiber are shown in Table 1.

TABLE 1

Mechanical Test Data for P4HB Monofilament Fiber

| Diameter, mm | Breaking Strength, Kgf | Break Elongation |
|---|---|---|
| 0.165 | 1.80 | 26% |
| 0.150 | 1.80 | 30% |
| 0.100 | 1.00 | 29% |

In another preferred embodiment, the fiber is made from poly(butylene succinate) or copolymer thereof. Suitable monofilament fibers of poly(butylene succinate) or copolymer thereof can be produced by melt extrusion.

Pouches that can prevent rotation and migration of breast implants can be prepared from the fibers described above. Such pouches can be produced from slow and fast degrading fibers, degradable fibers of different molecular weights, fibers that are unoriented, partially oriented and fully oriented, fibers with different elongation to break values, tensile strengths and tensile modulus values, or combinations thereof.

E. Films

The pouches may comprise films, and more preferably films that have been perforated to make them porous. The pores of the perforated films preferably have pore diameters from 0.01 mm to 10 mm, and more preferably from 0.1 mm to 1 mm. In a particularly preferred embodiment, the perforated films have pores that are larger than 0.5 mm, even more preferably at least 0.8 mm. The density of the pores of the perforated films is preferably greater than 1 per square cm, but less than 50 per square cm. The films are preferably made from degradable thermoplastics, and even more preferably from degradable polyesters. The films are preferably made from the degradable materials listed in Section II.A above. In a preferred embodiment, the films are made from P4HB or copolymer thereof, or from poly(butylene succinate) or copolymer thereof. The weight average molecular weight of the polymers in the films is preferably 10 kDa to 1,200 kDa, but is more preferably 50 kDa to 600 kDa. The films may be unoriented, partially oriented, mono-axially oriented or bi-axially oriented. The elongation to break of the films can be from 3-1,100%, but is more preferably 15%-300%. The thickness of the films is preferably from 0.01 mm to 10 mm. The burst strength of the films, including the perforated films, is preferably from 1-100 Kgf. The films may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The films of the pouch may have different degradation rates in vivo. Some films may degrade quickly while other films may degrade slowly. In another embodiment, the films comprise an additive or bioactive agent. The films can be produced by any suitable method, including melt extrusion, compression molding, injection molding, and solvent casting. In another embodiment, the films may be laminated or thermoformed. In one embodiment, the films may be laminated and then the laminated article perforated and used to form a pouch.

Pouches that can prevent rotation and migration of breast implants can be prepared from the films described above. Such pouches can be produced from slow and fast degrading films, films of different molecular weights, films with different degrees of orientation, films of different thicknesses, and films that are perforated, laminated or thermoformed, or combinations thereof.

F. Foams

The pouches may comprise foams. The foams are preferably made from degradable thermoplastic polymers, and even more preferably from degradable thermoplastic polyesters. The foams are preferably made from the degradable materials listed in Section II.A above. The foams can be made by any suitable method, including melt foaming and solution foaming, including particulate leaching. In a preferred embodiment, the foams are made from P4HB or copolymer thereof or poly(butylene succinate) or copolymer thereof. The foams may optionally be cross-linked. Preferably the polymers of the foams have weight average molecular weights of 10 kDa to 1,200 kDa, but more preferably 50 kDa to 600 kDa. The foams may have open cell or closed cell structures. In one embodiment, the foams have an open cell content of at least 10%, preferably at least 25%, and more preferably at least 50%. The cell sizes may be up to 5 mm. The densities of the foams are preferably less than 1 g/cm$^3$, more preferably less than 0.75 g/cm$^3$, and even more preferably less than 0.5 g/cm$^3$. The thicknesses of the foams may be from 0.01 mm to 10 mm. The foams may comprise additives or bioactive agents. The foams may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. In another embodiment, the foams comprise an additive or bioactive agent.

Pouches that can prevent rotation and migration of breast implants can be prepared from the foams described above. Such pouches can be produced from foams with open or closed cell structures, varying cell sizes and densities, different molecular weights, and different strength retention profiles.

G. Textiles

The pouches may comprise textiles. The textiles are preferably made from degradable thermoplastic polymers, and even more preferably from degradable thermoplastic polyesters. The textiles are preferably made from the degradable materials listed in Section II.A above. In a preferred embodiment, the textiles are made from P4HB or copolymer thereof, or poly(butylene succinate) and copolymers thereof.

The thicknesses of the textiles may be from 0.01 mm to 10 mm. The textiles preferably have an average pore size diameter from 75 µm to 5 mm, but more preferably from 500 µm to 5 mm, and even more preferably from 800 µm to 5 mm. Preferably the polymers and fibers used to make the textiles have weight average molecular weights of 10 kDa to 1,200 kDa, but more preferably 50 kDa to 600 kDa. The burst strength of the textiles is preferably 0.1 Kgf to 100 Kgf, but more preferably 1 Kgf to 50 Kgf. In embodiments, the textiles may have an elasticity of 15-75%, 30-65%, 8-20%, or 5-25%, wherein the elasticity is measured as the percent increase of an area of the textile when the area is subject to deformation in ASTM burst method D6797-02. The textiles may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The pouch may be formed from more than one textile, and the textiles used to form the pouch may degrade at different rates.

The pouches may be formed from woven and knitted textiles, or may be formed from non-woven textiles.

Woven and Knitted Textiles

In one embodiment, the textiles may be produced from monofilament fibers, multifilament fiber, yarn, or combinations thereof. The textiles may be produced from the fibers described in Section II.D above. The fibers may be unoriented, partially oriented, highly oriented or combinations thereof. The textiles may be knitted, woven, or braided from the fibers. The textiles may also be made from the fibers by crocheting. A particularly preferred textile for use in preparing the pouches is a warp knit mesh. In embodiments, the textiles with a thickness of 0.5-10 mm, and more preferably 0.75-3 mm may be used to make the front of a pouch. In another embodiment, textiles with a thickness of 0.2-0.6 mm, and more preferably 0.2-0.4 mm, may be used to make the back of the pouch. In another embodiment, textiles with an elasticity of 15-75% or 30-65% may be used to prepare the front of the pouch, and textiles with an elasticity of 5-25% or 8-20% may be used to prepare the back of the pouch, wherein the elasticity is measured as the percent increase of the area when the area is subject to deformation in ASTM burst method D6797-02 using a round ball.

In other embodiments, the textiles used to make the back, front bottom, and front top of the pouch have average pore diameter ranges of 0.5-3 mm, 0.5-1 mm, and 0.1-1 mm, wherein the front bottom of the pouch is the area placed in the lower pole nearest to the patient's skin, and the front top of the pouch is the area placed in the upper pole nearest to the patient's skin.

In a preferred embodiment, the textile is a mesh made from P4HB monofilament fiber, or fiber comprising poly (butylene succinate) or copolymer. In a more preferred embodiment, the P4HB monofilament mesh or mesh comprising poly(butylene succinate) or copolymer thereof, has a knitted or woven structure. A particularly preferred P4HB monofilament mesh has substantially one or more of the following properties: an average pore diameter of 500 µm to 3 mm, a pore diameter of approximately 500-1,000 µm, thickness of 0.2-10 mm, 0.2-5 mm, or 0.4-0.8 mm, areal density of 40-190 g/m$^2$ or approx. 140-190 g/m$^2$, suture pullout strength of 1-7 kgf, or 4-7 kgf, and a burst strength of 20-26 Kg or 0.1-30 kgf/cm$^2$. A preferred mesh comprising poly(butylene succinate) or copolymer thereof, has one or more of the following properties: (i) a suture pullout strength of at least 10 N, 1-7 kgf, or at least 20 N, (ii) a burst strength of 0.1 to 100 kgf, more preferably between 1 to 50 kgf, or greater than 0.1 kPa, (iii) a thickness of 0.5-10 mm, more preferably between 0.05-5 mm, (iv) an areal density of 5 to 800 g/m$^2$, (v) a pore diameter of 5 µm to 5 mm, or more preferably 100 µm to 1 mm, or (vi) an average pore diameter of 0.1-3 mm. The textiles comprising P4HB monofilament mesh or poly(butylene succinate) or copolymer thereof with an elasticity of 15-75% or 30-65% may be used to prepare the front of the pouch, and textiles comprising these polymers with an elasticity of 5-25% or 8-20% may be used to prepare the back of the pouch, wherein the elasticity is measured as the percent increase of the area when the area is subject to deformation in ASTM burst method D6797-02 using a round ball. A more preferred mesh comprising poly(butylene succinate) or copolymer thereof, has one or more of the following properties: (i) a suture pullout strength of 1 kgf to 20 kgf or 1-7 kgf, (ii) a burst strength of 1 to 50 kgf, more preferably 5 to 30 kgf, and even more preferably 0.1-30 kgf/cm$^2$ (iii) a thickness of 0.2-0.6 mm, 0.5-10 mm, or 0.1 to 1 mm, (iv) areal density of 40-190 g/m$^2$ or 100 to 300 g/m$^2$, and (v) pore diameter 100 µm to 1 mm. An even more preferred mesh comprising poly(butylene succinate) or copolymer thereof, has one or more of the following properties: a pore diameter of 500±250 µm, thickness of 0.4±0.3 mm, areal density of approx. 182±50 g/m², suture pullout strength of 5.6±2 kgf, and a burst strength of at least 3 kgf, and more preferably at least 6 kgf. A preferred textile comprising poly(butylene succinate) or copolymer thereof is a monofilament knitted mesh.

Suitable P4HB monofilament meshes for preparing the pouches may be prepared according to the following procedure: P4HB Monofilament fibers from 49 spools, prepared as described in Section II.D, are mounted on a creel, aligned side by side and pulled under uniform tension to the upper surface of a "kiss" roller. The "kiss" roller is spun while semi-immersed in a bath filled with a 10% solution of TWEEN® 20 lubricant. The TWEEN® 20 lubricant is deposited on the surface of the sheet of fiber. Following the application of TWEEN® 20, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scoring. The P4HB monofilament mesh produced according to this method is scored ultrasonically with water, heat set in hot water, and then washed with a 70% aqueous ethanol solution. A similar procedure may be used to prepare a monofilament mesh of poly(butylene succinate) or copolymer thereof.

Non-Woven Textiles

In another embodiment, the textiles may be produced directly from the degradable materials listed in Section II.A. In one preferred embodiment, the textiles have a non-woven structure. More preferably, the non-woven structure is dry-spun. Suitable methods to produce the textiles directly from degradable materials, preferably thermoplastic polymers and thermoplastic polyesters, include melt blowing, electrospinning, centrifugal spinning, spun bonding, and solvent spinning, including dry spinning. Dry spinning is a particularly preferred method for producing the textiles. The textiles may comprise an additive or bioactive agent. Dry spun textiles have a non-woven structure, as well as textiles produced by melt blowing, electrospinning, centrifugal spinning, spun bonding, and dry spinning.

In another preferred embodiment, the textile is a non-woven made from P4HB, or poly(butylene succinate) or copolymer thereof, preferably by solution spinning (also known as dry spinning). Suitable dry spun fibers of P4HB, or poly(butylene succinate) or copolymer thereof, may be produced by dissolving P4HB or poly(butylene succinate) or copolymer thereof, in a solvent to form a polymer solution. Suitable solvents include chloroform, methylene chloride, acetone, and THF. A particularly suitable polymer solution for P4HB is an 8% w/v solution of P4HB in chloroform. The polymer solution may be transferred to a solvent reservoir connected to a nozzle that is aimed at a collector. Dry spun fibers are collected when the polymer solution is injected or pumped into a stream of accelerated gas exiting the nozzle. Suitable dry spun equipment has an inner and a concentric outer nozzle, which creates a low-pressure region near the orifice of the inner nozzle. A suitable gas is compressed air. The collector may be stationary, and the nozzle moved in order to form a non-woven at the collector. However, more preferably, the collector can be rotated and moved in all directions in order for the collector to be completely covered by dry spun fiber, and if desired, to form a uniform coating of dry spun fibers on the collector. Generally, however, the distance between the collector and the nozzle is not varied significantly. The collector is preferably in the shape of a breast implant such that a pouch comprising dry spun fibers can be formed on the collector. The non-woven pouch, so formed, will then be of appropriate dimensions to encase a breast implant of the same dimensions as the collector. In one embodiment, the dry spun fibers have average diameters ranging from 0.01 µm to 50 µm. A particular advantage of solvent spinning P4HB fibers, and fibers of poly(butylene succinate) and copolymers thereof, rather than melt spinning, is that the weight average molecular weight of the polymer does not decrease by more than 10%, and even more preferably does not decrease by more than 5%, during spinning.

Textile Compositions and Properties

Pouches that can prevent rotation and migration of breast implants can be prepared from the woven, knitted and non-woven textiles described above. Such pouches can be produced from slow and fast degrading textiles, woven and non-woven textiles, knitted textiles, warp knitted textiles, degradable textiles of different molecular weights, textiles made from unoriented, partially oriented and fully oriented fibers, textiles made from monofilament fiber, multifilament fiber, yarn, and combinations thereof, textiles made directly from degradable materials, including by electrospinning, melt-blowing, solvent spinning including dry spinning, centrifugal spinning and spun-bonding, and textiles with different burst strengths, or combinations of the above.

In one embodiment, the pouch comprises an auxetic structure, and preferably an auxetic mesh.

In one embodiment, the textile may comprise a bioactive agent. The bioactive agent may be coated on the textile, the bioactive agent may be contained within the textile, or a combination thereof. In a preferred embodiment, the bioactive agent may be applied to the textile by spraying the textile with a solution of the bioactive agent or dip coating the textile in a solution of the bioactive agent. In another preferred embodiment, the textile comprising the bioactive agent may be formed directly in one step. For example, a solution of polymer and bioactive agent may be solution spun, dry spun or electrospun to form a textile comprising the bioactive agent. In a particularly preferred embodiment, the pouch may be formed from a P4HB textile, or textile of poly(butylene succinate) or copolymer thereof, coated with one or more bioactive agents, or by forming the P4HB textile, or textile of poly(butylene succinate) or copolymer thereof, comprising the one or more bioactive agents in one step, for example, by melt or solution processing, dry spinning, solvent spinning, centrifugal spinning, spun-bonding, melt-blowing, melt spinning or electrospinning. In a preferred embodiment, the textile used to form the pouch is a P4HB textile, or textile of poly(butylene succinate) or copolymer thereof, comprising one or more antibiotics.

III. Methods of Manufacturing Pouches to Limit Movement of Breast Implants

A variety of methods can be used to manufacture the pouches, and several different examples of pouches to limit rotation and migration of breast implants are described herein. The pouches limit the rotation of breast implants after implantation in the patient. In embodiments, pouches prevent breast implants from rotating more than 45 degrees, and more preferably more than 30 degrees, after implantation. In other embodiments, the pouches limit migration of breast implants after the breast implant is placed in the pouch, and the pouch is implanted in the patient. Limiting migration means that the pouch can be used to prevent the breast implant from migrating a threshold distance after implantation. In embodiments, the threshold distance is 5 cm, and more preferably 3 cm or 1 cm. Prevention of migration is important to prevent pocket stretch, ptosis, and lateral displacement of breast implants.

The pouches may have three-dimensional shapes. Preferably, the pouch has the same shape, identical shape, or a similar shape, as the breast implant that is placed inside the pouch. The pouches are preferably just slightly larger than the breast implant in order to allow insertion of the breast implant into the pouch.

In other embodiments, the pouches have an elasticity that allows a tight fit to be formed between the pouch and the breast implant. Preferably, the volume of the pouch is no more than 20% larger than the breast implant that will be placed inside the pouch, more preferably no more than 10% larger than the breast implant that will be placed inside the pouch, and even more preferably no more than 5% larger than the breast implant that will be placed inside the implant. Preferably, the volume of the pouch is between 150-800 cc, and more preferably between 165-800 cc. Preferably the width of the base of the pouch is 7.4-17.2 cm, and more preferably 9-16.5 cm, and has a projection ranging between 4 and 8.5 cm, and more preferably 4.2-7 cm.

The pouch may have a dome shape, round shape or anatomical shape. The pouch may comprise surfaces with flat, round, curved or anatomical shapes. The shape of the pouch preferably follows the contours of the breast implant that will be inserted in the pouch. The breast implants may include silicone and saline breast implants, anatomic and round breast implants, and surface textured and non-textured breast implants. Non-limiting examples of breast implants include: (i) Mentor's MemoryShape® breast implants, MemoryGel® breast implants, and Spectrum® breast implants; (ii) Allergan's Natrelle® breast implants, including their gummy breast implants, Inspira® responsive, soft touch and cohesive breast implants, Natrelle® 410 anatomical implants, Natrelle® saline-filled breast implants, and Biocell™ breast implants; (iii) Sientra's Opus™ breast implants, including their smooth round, textured round and textured shaped, high strength cohesive breast implants, HSC and HSC+; (iv) Arion Laboratories' Monobloc® silicone and hydrogel-CMC breast implants; (v) Cereplas Cereform® breast implants; (vi) Establishment Labs' Motiva® breast implants, including their Ergonomix™ and Round breast implants; (vii) GC Aesthetics' Eurosilicone® and Nagor® breast implants, including Impleo™ CoGEL™, Round Collection by Eurosilicone®, The Matrix by Eurosilicone®, GFX™ by Nagor®, and RGI™ by Nagor® breast implants; (viii) Groupe Sebbin's inflatable, cohesive round, high cohesive round, short anatomical and tall anatomical breast implants; (ix) Guangzhou Wanhe Plastic Materials' Snow. Lambe, Crystal.Lambe, and Lambe breast implants; (x) Hans Biomed's BellaGel breast implants; (xi) Ideal Implant Incorporated's Ideal Implant® breast implants; (xii) Polytech Health and Aesthetics' Mesmo®, Polytxt®, Microthane®, SublimeLine® and Diagon\Gel® 4 Two breast implants; and (xiii) Silimed breast implants including conical, round and anatomical shapes. Additional examples of breast implants for use with embodiments of the subject invention are disclosed by Maxwell and Gabriel, The evolution of breast implants, Plast. Reconstr. Surg. 134:12S, 2014, and references therein, U.S. Pat. No. 10,052,192 to Schuessler, U.S. Pat. No. 6,074,421 to Murphy, U.S. Pat. No. 5,007,929 to Quaid, U.S. Pat. No. 8,211,173 to Keller, U.S. Pat. No. 4,960,425 to Yan, U.S. Pat. No. 4,380,569 to Shaw, U.S. Pat. No. 5,902,335 to Snyder, U.S. Pat. No. 3,293,663 to Cronin, U.S. Pat. No. 4,863,470 to Carter, U.S. Pat. No. 4,773,909 to Chaglassian, U.S. Pat. No. 6,074,421 to Murphy, U.S. Pat. No. 8,377,127 to Schuessler, and U.S. Pat. No. 8,043,373 to Schuessler.

In embodiments, the shape of the pouch preferably drapes the inserted breast implant. The size and shape of the pouch used in a procedure may be based upon the surgeon's and patient's choice of the breast implant size and shape, and the need to match those requirements closely to the pouch size so that the implant cannot rotate when inserted in, and secured in, the pouch. In an embodiment, the pouch has elasticity that makes it possible to easily insert the breast implant into the pouch with a tight fit. Preferably, the pouch is formed with a front area of the pouch having an elasticity of 15-75% or 30-65%, and the back area of the implant having an elasticity of 5-25% or 8-20%, wherein the elasticity is measured as the percent increase of the area when the area is subject to deformation in ASTM burst method D6797-02 using a round ball. In this embodiment, the front area of the pouch is the area placed just beneath the patient's skin, and the back area of the pouch is the area placed on the chest wall.

Preferably the pouches are porous, or become porous after implantation, and even more preferably the pouches are macro-porous or become macro-porous after implantation. In a preferred embodiment, the pouches comprise pores with average pore diameters of at least 100 μm, more preferably at least 250 μm, and even more preferably at least 500 μm. A particularly preferred pore diameter is 800 μm±300 μm. A particularly preferred pore size is 0.64 mm²±0.3 mm². The pouches may be prepared from porous materials, or they may be prepared from non-porous materials. In embodiments, pouches prepared from non-porous materials are then perforated.

In one embodiment, a pouch for fixation of a breast implant may be prepared with different pore sizes in different areas of the pouch. Preferably, the pouch is prepared with larger pores around the perimeter of the pouch and on the back of the implant (which contacts the chest wall after implantation), and smaller pores on the top front side of the pouch (which is placed in the upper pole of the breast under the skin of the patient). The larger pores on the back of the pouch improve the drapeability of the pouch. The smaller pores on the top front of the pouch increase the surface area available for coating with fat, and allow delivery of more fat to the upper pole of the breast. In a preferred embodiment, the average pore sizes of the pouch are: 0.5-3 mm on the back of the pouch, 0.1-1 mm on the top front of the pouch, and 0.5-1 mm on the bottom front of the pouch (which is placed in the lower pole of the breast under the skin of the patient).

In a preferred embodiment, the front of the pouch (that is placed beneath the patient's skin) has a thickness of 0.5-10 mm, and the back of the pouch (that is placed next to the chest wall) has a thickness of 0.2-0.6 mm, and more preferably from 0.2-0.4 mm. Pouches with thicker front areas make it possible to avoid the formation of ripples and indentations on the patient's skin caused by ripples present on breast implants, and reduce or eliminate the palpability of the breast implant. Use of pouches with thicker front areas is particularly important in patients where the skin is thin, or in patients where excessive amounts of tissue have been removed such as in radical mastectomy procedures.

The pouches are preferably made from resorbable polymers, more preferably from resorbable fibers, and even more preferably from resorbable fibers that degrade in less than 5 years, more preferably in less than 2 years, and even more preferably in less than 1 year. The pouches may comprise fibers with fast and slow rates of degradation.

In another embodiment, the pouches are formed by 3D-printing. Suitable methods for 3D-printing the pouches include fused filament fabrication, fused pellet deposition, melt extrusion deposition, selective laser melting, printing of slurries and solutions using a coagulation bath, and printing using a binding solution and granules of powder. Preferably, the pouches are 3D-printed using P4HB or poly(butylene succinate) or copolymer thereof.

In a preferred embodiment, there is an opening in the pouch to allow insertion of the breast implant. The opening may be made after the pouch has been constructed, or during construction of the pouch. The opening may be made in a component of the pouch, such as the base or rear of the pouch, prior to assembly of the pouch. The opening can be a slit in the pouch, preferably in the base of the pouch or on the side of the pouch. The slit can be reinforced. The slit can be elasticated. The slit can be linear, or curve shaped. In an embodiment, the pouch can comprise a cover or seal placed over the opening where the breast implant is inserted.

In a preferred embodiment, the slit will contact the chest wall when the pouch is implanted. In such an embodiment, the slit is placed in the back or rear of the pouch, that is placed on the chest wall as shown, for example, in FIGS. 19A-19C. This orientation of the slit is preferred since it prevents the breast implant from being released from the pouch in situ. Even more preferably, the pouch comprises a slit in the back of the pouch and incorporates tabs to allow fixation to the chest wall such that the slit of the pouch will be on the chest wall when implanted.

The manufactured pouches preferably have an endotoxin content of less than 20 endotoxin units making them suitable for implantation in a patient.

The pouches may comprise the additives listed in Section II.B and the bioactive agents listed in Section II.C.

Pouches Limiting Breast Implant Rotation by a Cinching Mechanism

In one preferred embodiment, the pouches are designed to limit rotation of breast implants using a cinching mechanism. A diagram of a pouch 10 with a cinching mechanism 12 is shown in FIG. 1. The pouch 10 comprises a slit 14 for insertion of a breast implant, and a draw cord 12 running around the perimeter of the pouch that can be tightened to limit rotation of a breast implant inside the pouch. In an embodiment, pouches with a cinch mechanism can be prepared by molding processes. In these processes, fiber-based structures, films, foams, 3D-printed structures, and combinations thereof, are molded into shapes to accommodate breast implants. Fiber-based structures include structures formed by melt-blowing, solution spinning, dry spinning, electrospinning, centrifugal spinning, melt spinning, knitting, weaving, braiding, entangling of fibers, 3D-printing, as well as embedded fibers in other structures such as foams, films, laminates, and fibers coated with films and foams. Fiber-based structures may comprise monofilament fibers, multifilament fibers, hollow fibers, and yarns. Fiber-based structures include non-woven structures, knitted structures, braided structures, textiles, fabrics, and woven structures. Preferred fiber-based structures are (i) knitted monofilament meshes, and even more preferably a knitted monofilament mesh comprising P4HB or copolymer thereof, or poly (butylene succinate) or copolymer thereof, and (ii) dry spun nonwovens, and even more preferably P4HB dry spun nonwovens or dry spun nonwovens of poly(butylene succinate) or copolymer thereof.

In a preferred embodiment, the pouches with cinch mechanism (as shown in FIG. 1) are prepared by thermoforming fiber-based structures, foams, films, or laminates. In a particularly preferred method, the pouches are formed using a mold substantially in the shape, or part of the shape, of a breast implant. The mold may, for example, be dome shaped, round, spherical, semi-spherical, or an anatomical shape. Preferably the mold is the same size or slightly larger than the breast implant, but preferably the volume of the mold is not more than 20% larger, more preferably not more than 10% larger, and even more preferably not more than 5% larger than the breast implant. In one embodiment, the mold is made from metal.

Figure 2A:
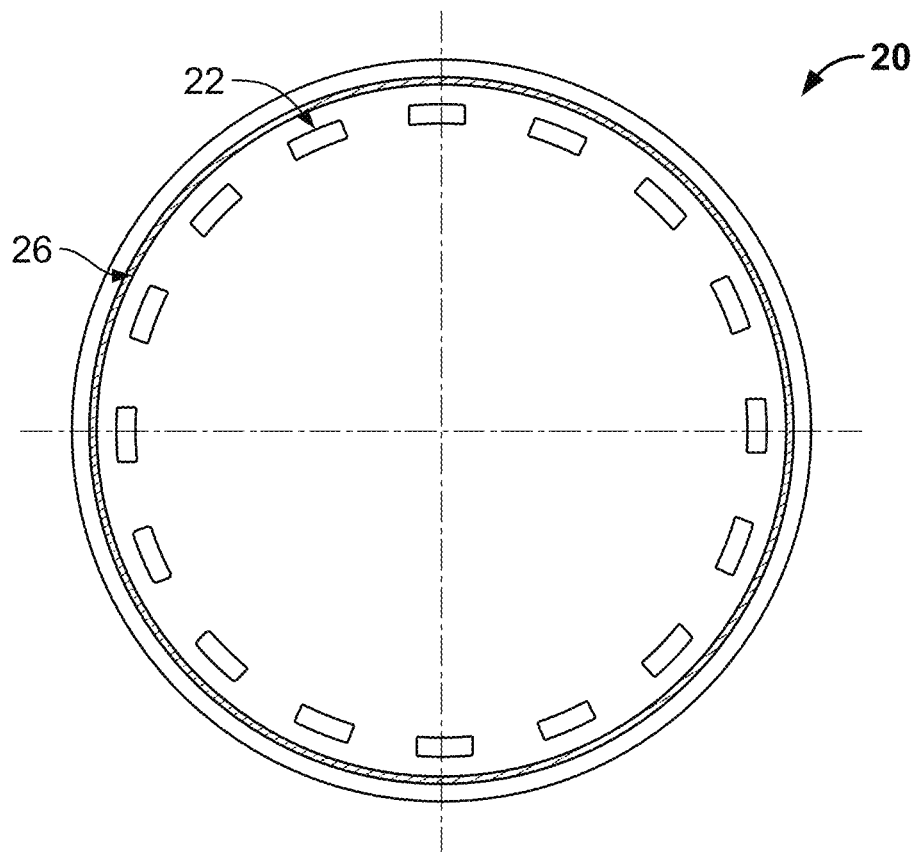
FIG. 2A shows the front half of the breast implant pouch used to prepare the implant shown in FIG. 1 comprising a circular mesh with rectangular holes cut in the mesh around its perimeter.
Figure 2B:
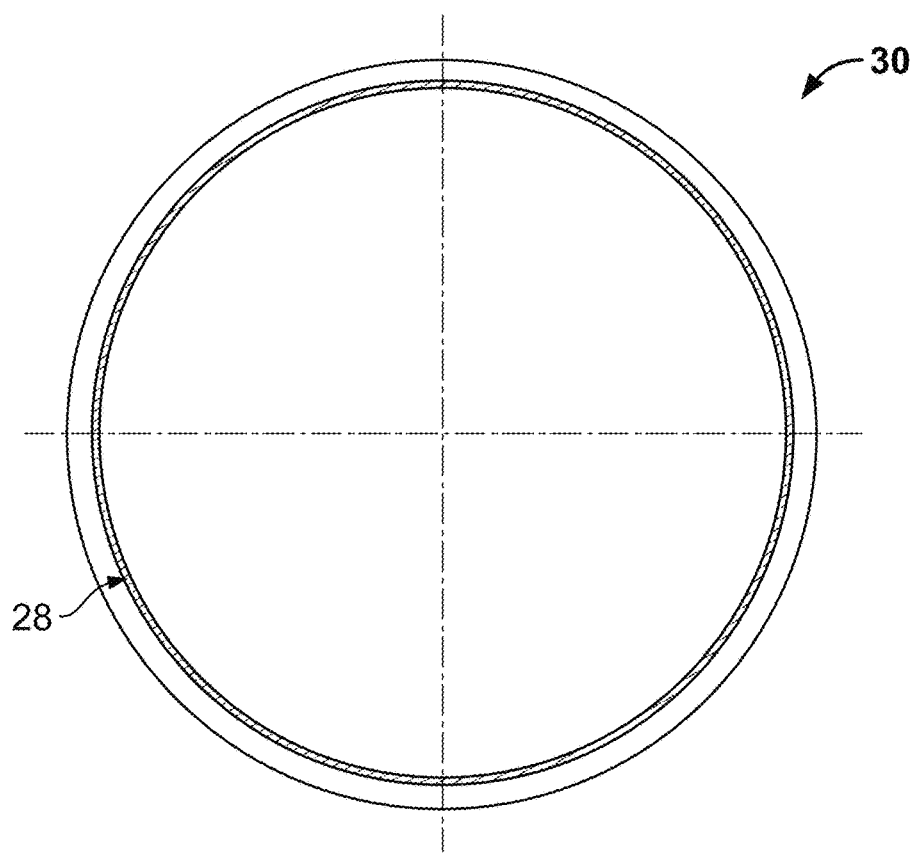
FIG. 2B shows the back half of the breast implant pouch used to prepare the pouch implant shown in FIG. 1 comprising a circular mesh with a seal area for bonding with the front half of the breast implant pouch shown in FIG. 2A.

With reference to FIGS. 2A-2B, in a preferred embodiment, the method of making the pouch for a breast implant with a cinch mechanism comprises the steps of forming a front half 20 of a pouch and a back or rear half 30 of a pouch, and joining the front half and back half together. In this embodiment, the front half 20 of the pouch refers to the part of the pouch that will be placed in the anterior position in the patient, and the back half 30 of the pouch refers to the part of the pouch that will be placed in the posterior position in the patient. The back half 30 of the pouch may also be referred to as the rear of the pouch.

The front half 20 of the pouch encompasses most, and preferably all, of the projection of the breast implant from the chest of the patient. The front and back halves of the pouch may be joined by any suitable method, including sewing and welding. For example, the halves may be joined using an ultrasonic spot welder or using a knitting machine.

In one embodiment, the front half of the pouch with a cinch mechanism is made by thermoforming. Preferably, a fiber-based structure is thermoformed to make the front half of the pouch. The fiber-based structure is preferably porous. The front half of the pouch may also be thermoformed from a non-fiber based structure, such as a film, laminate, or foam, or structure comprising a combination of fibers, films, or foams. The front half of the pouch may also be thermoformed from a non-porous structure, and later perforated. In a preferred embodiment, the front half of the pouch is made by thermoforming a knitted mesh, more preferably a knitted monofilament mesh, and even more preferably a knitted monofilament mesh comprising P4HB or copolymer thereof, or comprising poly(butylene succinate) or copolymer thereof. In a particularly preferred embodiment, the pouch is formed by joining a front half of a pouch made by thermoforming P4HB knitted monofilament mesh, to a back half of a pouch made from P4HB knitted mesh, or by joining a front half of a pouch made by thermoforming a monofilament mesh of poly(butylene succinate) or copolymer thereof to a back half of a pouch made from a mesh of poly(butylene succinate) or copolymer thereof. The P4HB and poly(butylene succinate) or copolymer thereof monofilament fibers of the mesh used to prepare the front and back halves are preferably oriented, that is, the P4HB and poly(butylene succinate) or copolymer thereof monofilament fibers have been stretched during their manufacture.

The front half of the pouch with a cinch mechanism may be thermoformed from a P4HB monofilament knitted mesh, prepared as described in Section II.G above, by placing the mesh over a suitable metal mold, such as a half-dome mold, and heating the mesh under tension. Suitable conditions for heating the P4HB mesh are 57° C. for 5 min. After heating to shape the mesh, the shaped mesh can be quenched, for example, in a cold-water bath. Suitable conditions for quenching are immersion in a cold-water bath set at 9° C. for 10 min. After quenching, the shaped front half of the pouch can be removed from the mold, and attached to a suitably sized back half to form the pouch.

The front half or back half of the pouch with a cinch mechanism, or both halves, may comprise an opening to allow insertion of the breast implant into the pouch. The opening may be inserted before or after the construction of the pouch. In one preferred embodiment, the opening is placed in the back half of the pouch. The opening is preferably made in the back half of the pouch prior to attaching it to the front half of the pouch. In another preferred embodiment, the opening is made after assembly of the pouch from the front and back halves. The latter opening may in one embodiment be a V-shaped opening prepared by the removal of a wedge shape from the pouch. An opening may be made in a pouch comprising P4HB knitted monofilament mesh, or monofilament mesh of poly (butylene succinate) or copolymer thereof, using a laser, or by another suitable cutting method.

The thermoformed pouches with cinch mechanisms may comprise suture straps so that the pouches can be anchored in place in the patient. Preferably the straps are placed around the perimeter of the pouch. Any number of straps may be incorporated, including 1, 2, 3, 4, 5, 6, 7, 8, 9, 10, 11, and 12, but more preferably 4 straps can be incorporated on the perimeter of the pouch spaced at 90 degrees from each other. In one embodiment, a pouch with straps may be prepared by forming a circular mesh, as described above, with straps placed around its perimeter, and joining it to a thermoformed mesh front half, also prepared as described above. Preferably the straps are made from P4HB monofilament mesh or mesh made from poly(butylene succinate) or copolymer thereof.

Various methods may be used to secure the breast implants inside the pouches. In one preferred embodiment, the pouch with the cinch mechanism comprises a draw cord that can be tightened to prevent rotation of the breast implant inside the pouch. Tightening the draw cord causes the pouch to cinch or slightly compress the breast implant, and limits rotation of the breast implant inside the pouch. In one embodiment, the draw cord is placed around the perimeter of the pouch, preferably, in an alternating pattern through slots in the perimeter of the pouch.

A pouch 10 with a draw cord 12 (see, e.g., FIG. 1) can be prepared using, for example, the following method steps: (i) a mesh is cut to form two circular shapes, a front half 20 and a back half 30, (ii) the front half 20 is further cut to insert a series of holes 22 around the perimeter for later insertion of a draw cord, and then thermoformed to form a semi-spherical 3D shape suitable for later insertion of a breast implant, (iii) the back half 30 shape is then attached to the front half shape to form the pouch, (iv) a slit 14 is inserted in the side of the pouch to allow insertion of a breast implant into the pouch, and (v) a draw cord 12 is laced around the perimeter of the pouch alternating through the holes 22 cut in step (ii) as illustrated in FIG. 1. Preferably, the mesh used in this method is a monofilament mesh, more preferably a warp knit monofilament mesh, and even more preferably a warp knit monofilament mesh comprising P4HB or copolymer thereof, or comprising poly(butylene succinate) or copolymer thereof. A P4HB monofilament knitted mesh may be thermoformed by molding the mesh in a hot water bath over a metal mold with the mesh under tension, and then quenching the mesh in a cold-water bath. The two halves of the mesh, the front and back halves, are preferably sewn or welded together to form the pouch in step (iii) above. Different sizes and shapes of pouches may be prepared by using molds of different sizes, including round shapes and anatomical shapes. The draw cord may, for example, be a monofilament, multifilament, braid, or tape. Suture straps for anchoring the pouch in the patient may also be incorporated into the pouch by cutting the mesh for the back half of the pouch in step (i) so that straps of mesh protrude from the perimeter of the circular mesh. Any number of suture straps can be included, including 1, 2, 3, 4, 5, 6, 7, 8, 9, 10, 11, 12, but more preferably four straps are included around the perimeter of the circular mesh at 90 degree intervals.

Figure 4A:
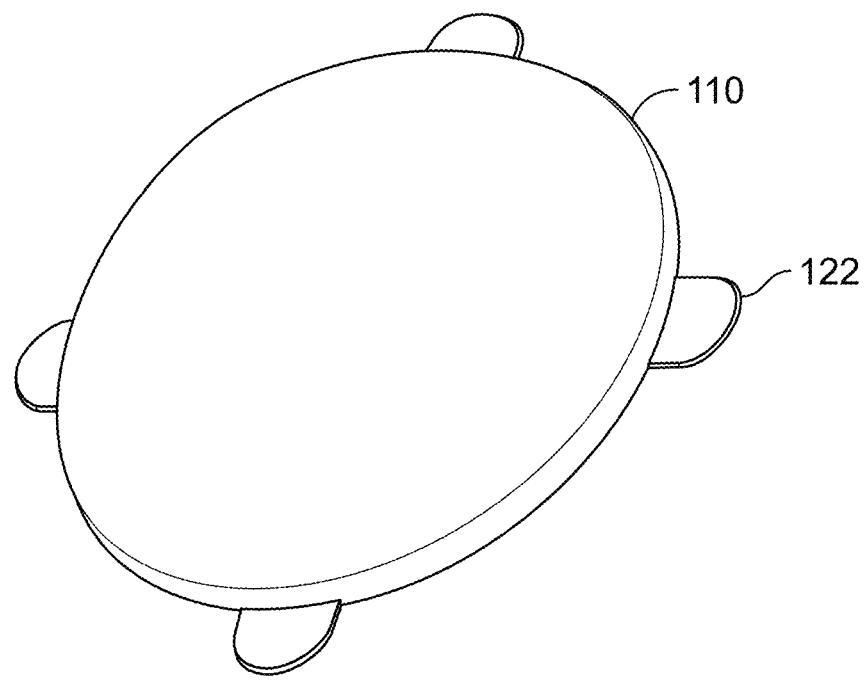
FIGS. 4A, 4B are isometric views of a pouch in accordance with another embodiment of the invention having four slots, with tabs from a breast implant located inside the pouch protruding through the slots.
Figure 4B:
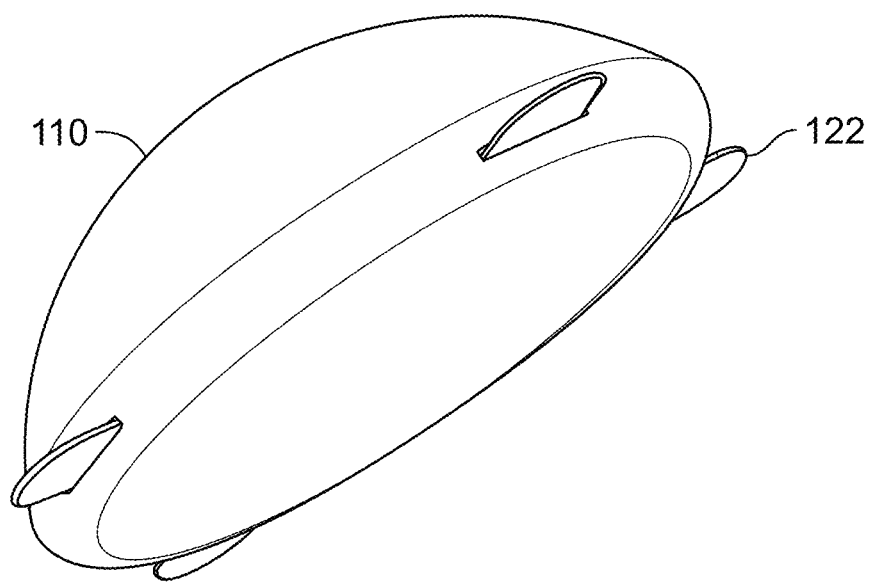

Pouches with Slots that Mate with Tabs of Tabbed Breast Implants to Limit Rotation of the Breast Implant In another preferred embodiment, a pouch 110 is designed for use with a tabbed breast implant, and mate with the tabs 122 of the breast implants to limit rotation of the breast implants. A diagram of a slotted pouch containing a tabbed breast implant is shown in FIGS. 4A, 4B with the tabs 122 of the breast implant protruding from the inside of the pouch 110, through the pouch slots, to the outside.

Figure 6:
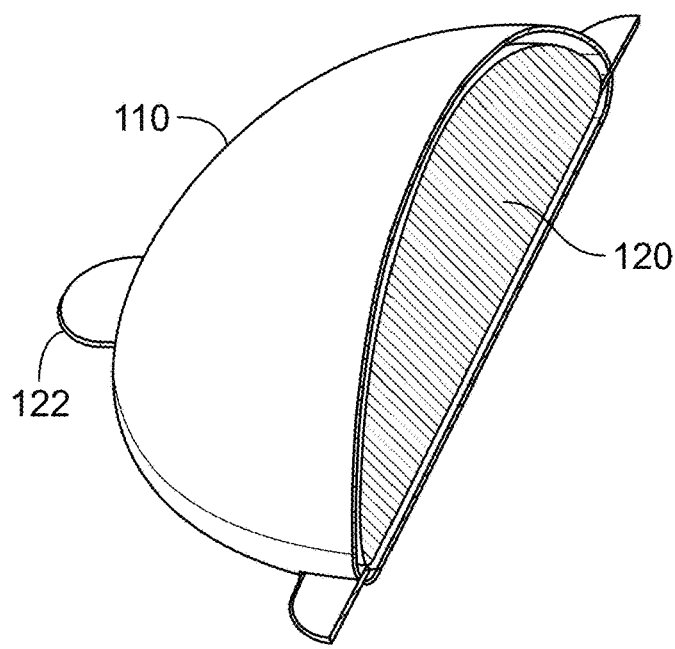
FIG. 6 is a cross-sectional view of the pouch shown in FIGS. 4A, 4B, containing a tabbed breast implant with the tabs of the breast implant protruding from the breast implant through slots in the pouch in accordance with another embodiment of the invention.

A cross-section of the slotted pouch 110 containing a tabbed breast implant 120 is shown in FIG. 6. A preferred method of making a pouch with slots that mate with tabs of a tabbed breast implant to limit rotation of the breast implant comprises the steps of: (i) solution spinning a nonwoven on a collector to form a pouch, (ii) cutting the nonwoven in order to remove it from the collector, and (iii) creating mating slots in the nonwoven pouch to receive tabs from a tabbed breast implant.

Figure 5:
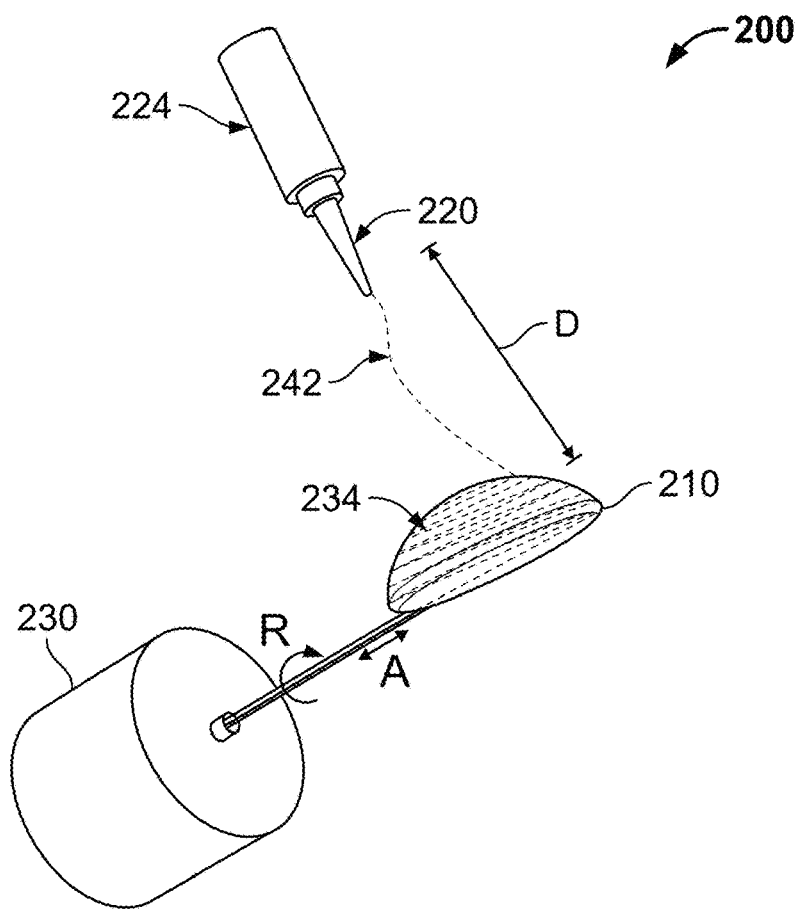
FIG. 5 is a diagram illustrating solution spinning equipment used to prepare a dry spun pouch in accordance with an embodiment of the invention.

With reference to FIG. 5, a suitable equipment set up 200 for solution spinning a pouch that can be used with a tabbed breast implant comprises a collector 210, a spray nozzle 220, a compressed gas line, a reservoir for a spinning solution 224, and a motor 230 that can either move the nozzle around the collector, or vice versa, in order to spray all the collector with fibers and preferably produce an even coating of fibers 234 on the collector. The collector 210 is preferably in the shape of the breast implant that will be inserted inside the pouch, and can, for example, be made from aluminum or stainless steel. The collector may, for example, be round, a sphere, a semi-sphere, or an anatomical shape. The volume of the collector is preferably 80-800 cm$^3$. The width of the collector is preferably 7.4-17.2 cm. A suitable nozzle for dry spinning has an inner and a concentric outer nozzle, which creates a low-pressure region near the orifice of the inner nozzle. Suitable spinning solutions can be prepared by dissolving polymers in volatile organic solvents. Suitable organic solvents include chloroform, methylene chloride, acetone, and THF. The concentration of the polymer in the solvent will vary depending upon the solubility of the polymer, and its solution viscosity. Preferred concentrations of the polymer in the solvent include 3-10% w/v. Dry spun fibers are deposited at the collector by pumping a polymer solution through the nozzle, and injecting it into a stream 242 of accelerated gas directed at the collector. The rate of injection of the polymer solution is preferably controlled by a pump drive. Suitable pump speeds will depend upon the particular polymer solution, and the equipment set up. Suitable sources of accelerated gas are compressed air, nitrogen and helium. Suitable pressures of the compressed gas include 5-3,500 kPa. In an embodiment, the compressed gas may be heated. In a preferred embodiment, the collector is kept at a fixed distance from the nozzle, but rotated (R) and moved axially (A) so that an even coating of dry spun fibers is deposited on the collector. A preferred distance (D) of the collector from the nozzle is 40-80 cm. In an embodiment, the collector may be rotated at 10-100 rpm, and more preferably 25-60 rpm. The average diameter of the dry spun fibers deposited at the collector is preferably 0.01-50 µm, and more preferably 5-30 µm. The preferred thickness of the fibers deposited on the collector should be sufficient to ensure the integrity of the pouch. In one embodiment, the thickness of the fibers deposited at the collector is 0.25-3 mm, and more preferably 0.5-1 mm. After collection of the dry spun fibers at the collector, the non-woven may be removed from the collector by cutting a slit in the non-woven. Preferably, a V-shaped slit is cut in the non-woven to allow removal of the non-woven pouch from the collector. The slit is preferably made in the non-woven pouch in a position where the same slit can be used to insert a breast implant inside the non-woven pouch. Slits may be cut in the non-woven using a sharp blade. Once the pouch has been removed from the collector, slots that will mate with tabs on a tabbed breast implant are cut in the pouch, preferably with a sharp blade. Preferably, the slots are located around the perimeter of the pouch. FIGS. 4A, 4B depict four slots cut in the perimeter of a pouch, and a tabbed breast implant inserted inside the pouch so that its tabs protrude through the slots. The number of slots cut in the pouch and their locations will preferably match the number and locations of the tabs on the tabbed breast implant. In one preferred embodiment, there are 1-6 tabs on the tabbed breast implant, and 1-6 mating slots on the pouch, and more preferably 4 tabs on the tabbed breast implant and 4 mating slots on the pouch as shown in FIGS. 4A, 4B.

A particularly preferred polymer for preparing a non-woven pouch is P4HB or copolymer thereof. Another particularly preferred polymer for preparing a non-woven pouch is poly(butylene succinate) or copolymer thereof. P4HB and poly(butylene succinate) or copolymer thereof may be dry spun without any significant loss of weight average molecular weight. In a preferred embodiment, the P4HB and poly(butylene succinate) or copolymer thereof do not lose more than 10% of their weight average molecular weights during dry spinning of a non-woven pouch.

Figure 8:
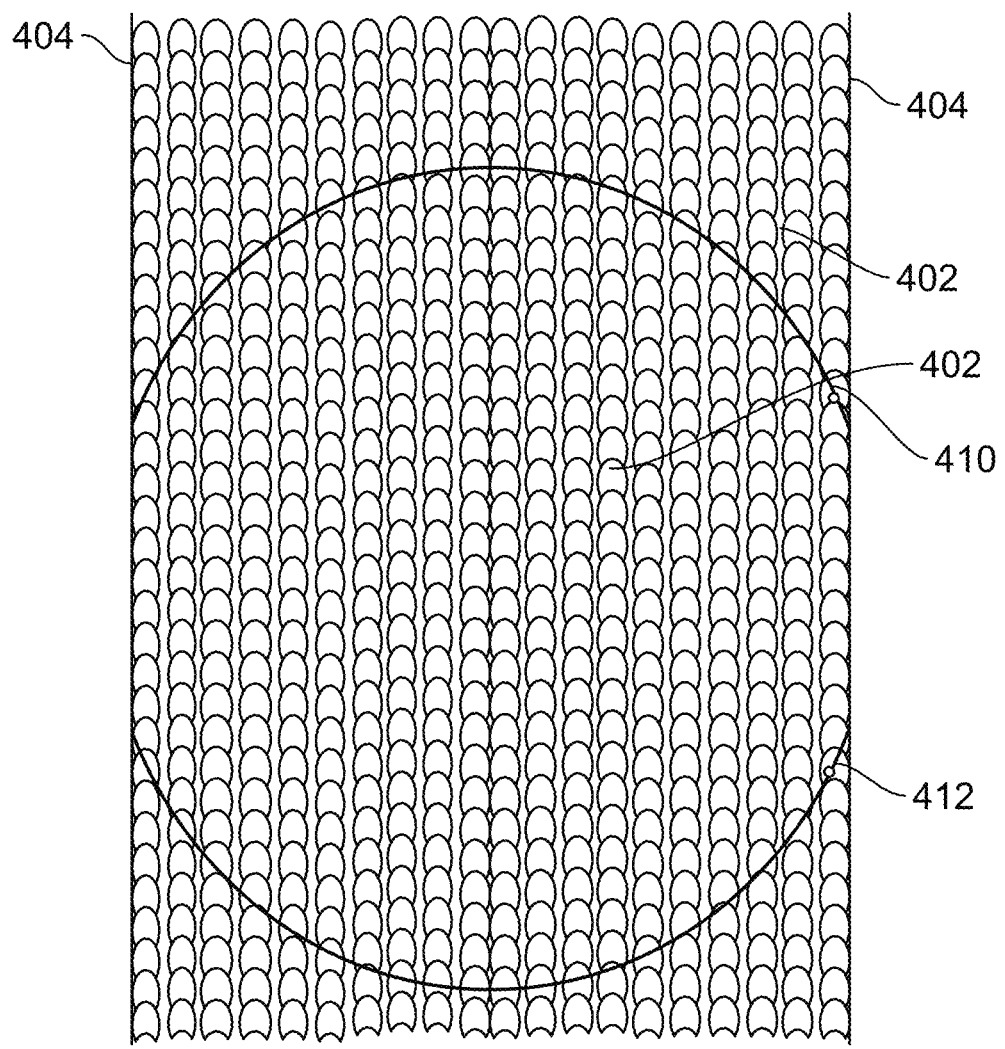
FIG. 8 is a diagram showing the loop knit pattern of a pouch for a breast implant in accordance with an embodiment of the invention, formed by knitting a front fabric and a back fabric separately, except at the two edges 404 where the fabric is knit simultaneously to join the front and back fabrics, and in the connected area 412 where the fabric is also knitted simultaneously to join the front and back fabrics with an open and closed stitch knit.
Figure 9:
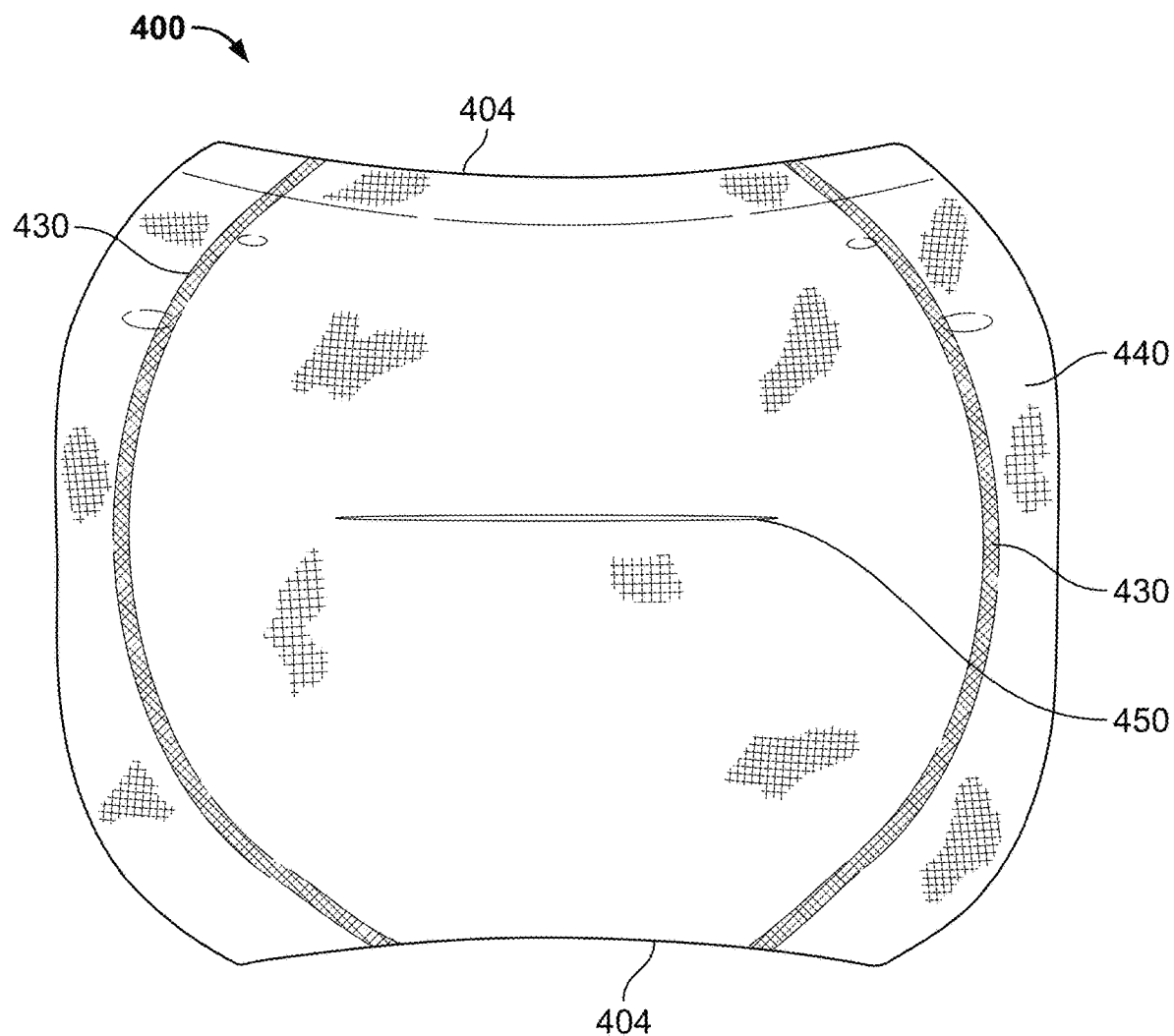
FIG. 9 shows a pouch formed from a tubular warp knitted structure in accordance with an embodiment of the invention.

Pouches Limiting Breast Implant Movement Prepared by Warp Knitting Using a Knitting Machine with a Double Needle Bed With reference to FIGS. 8, 9, in yet another preferred embodiment, a pouch for limiting the movement of a breast implant may be prepared by warp knitting using a knitting machine with a double needle bed. An example of a pouch 400 prepared using a knitting machine with a double needle bed is shown in FIG. 9. The pouch 400 may be formed by knitting a tubular construct 402, for example, with the loops shown in FIG. 8, but wherein sections of the tube are knitted together at the edges 404 and in the connected areas 410, 412 shown in FIG. 8 and the "knitted closure" region 430 shown in FIG. 9.

In one embodiment, a knitting machine is set up so that mesh is knit separately on the front and back beds of the knitting machine, except for the edges where fiber is knit simultaneously on the front and back beds to form a tubular structure. It is to be appreciated the enclosure is shown having an initial 2D or flattened sleeve construct. After the breast implant is placed within the enclosure, the enclosure takes a second 3D construct more closely in the shape of the breast implant itself. The pouch is preferably knit with closed loop stitches knit separately on the front and back beds. In embodiment, the upper and lower connected areas 410, 412 shown in FIG. 8 are also knit simultaneously on the front and back beds of the knitting machine. The connected areas 410, 412 or seams preferably comprise concave and convex shapes as shown in FIG. 8. In this manner, a pouch is formed in the tubular knit in the area located inside the connected area.

In embodiments, the connected areas or seams join two separate sheets together and form the perimeter of the cavity to hold the breast implant.

In embodiments, a single sheet is folded to form two sides of the pouch, and the connected areas or seams join the sides together and form the perimeter of the cavity to hold the breast implant.

After knitting, the tubular knit may be cut and trimmed to shape the pouch. Although the figures illustrate a particular shape of pouch and enclosure, the invention is not so limited except where specifically recited in the appended claims. The shape of the pouch may vary widely provided it can limit movement of the breast implant once implanted.

In a preferred embodiment, the pouch further comprises regions or areas 440 outside of the connected areas as shown in FIG. 9. These connected areas 430 can be used by the surgeon to fixate the pouch to tissue during implantation. Preferably, extension areas 440 are sutured or stapled to the patient's tissue.

With reference again to FIG. 9, a slit 450 may be cut on one side of the knitted pouch to create an opening for insertion of a breast implant into the pouch. The slit should be sufficiently wide to allow insertion of the breast implant. Preferably the slit is located in the rear (or back) of the pouch so as to be placed against the chest wall of the patient once implanted.

The pouch 400 is preferably knit with monofilament fiber. Preferably, the monofilament fiber has a diameter from 0.04 mm to 0.35 mm, but more preferably 0.05 to 0.2 mm. In a particularly preferred embodiment, the pouch is knit with monofilament fiber comprising P4HB or poly(butylene succinate) or copolymer thereof.

In an alternative embodiment, a warp knitted pouch may be prepared as described above using a double needle bed, but without knitting of the connected areas shown in FIG. 8. Instead of knitting the connected areas, the pouch may be formed by knitting a hollow tube, and using an ultrasonic welder to form heat seals in the connected areas shown in FIG. 8. A pouch is thus formed from a tubular knitted mesh by welding together the front and back meshes of the tubular knit, followed by trimming. Preferably, the tubular mesh is welded so the connected areas comprise concave and convex shapes as shown in FIG. 8, but there is no particular limitation on the shape of the pouch provided it can limit movement of the breast implant once implanted in a patient.

As described above, a slit may be introduced in the pouch to allow the introduction of the breast implant into the pouch. The pouch is preferably knit with monofilament fiber. Preferably, the monofilament fiber has a diameter from 0.04 mm to 0.35 mm, but more preferably 0.05 to 0.2 mm. In a particularly preferred embodiment, the pouch is knit with monofilament fiber comprising P4HB or poly(butylene succinate) or copolymer thereof.

Figure 10:
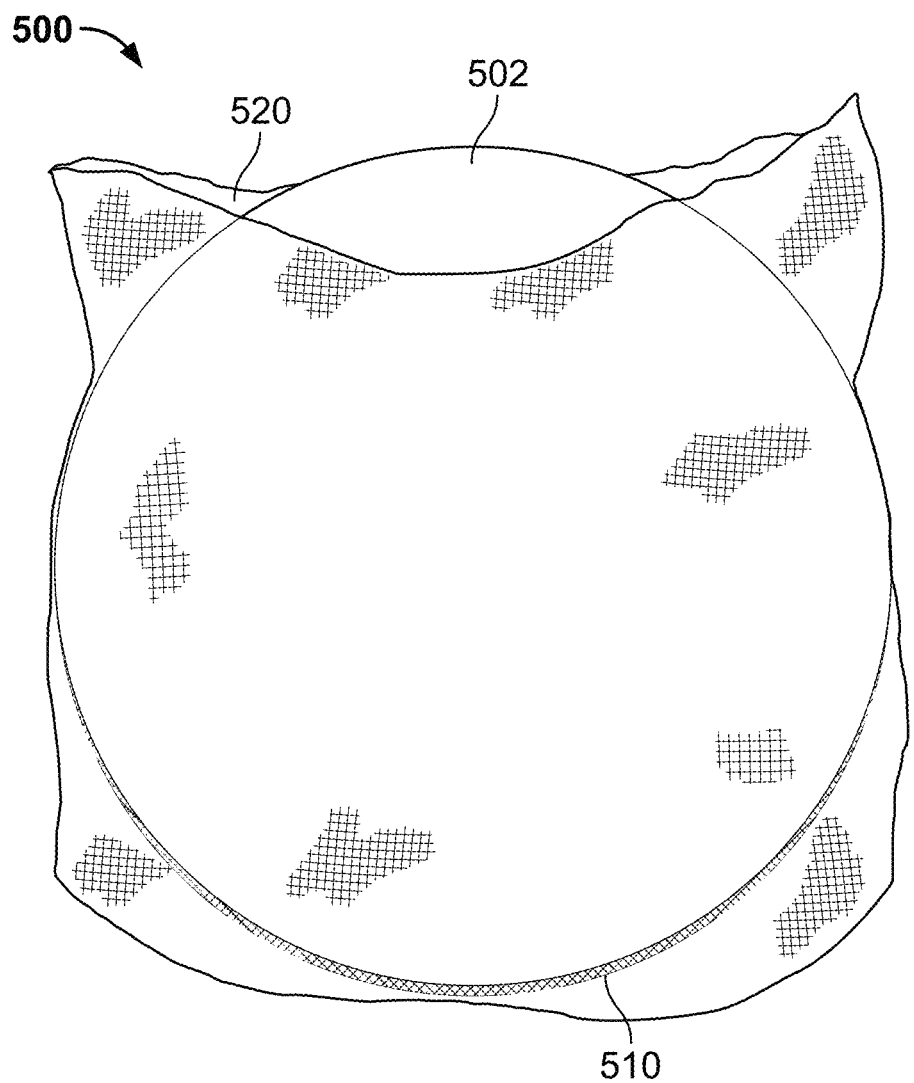
FIG. 10 shows a breast implant in a pouch formed from a warp knitted mesh structure of poly-4-hydroxybutyrate fiber in accordance with an embodiment of the invention including a knitted seal at one end that permits uniform stretching of the pouch.

In yet another embodiment, and with reference to FIG. 10, a pouch 500 for limiting movement of a breast implant 502 has a semi-circular shape. In a sense, the pouch has a pita pocket-like shape.

It may be prepared from a tubular knit, produced for example as described above, and include a concave-shaped lower end 510 and a slit 520 or opening at the upper end of the pouch instead of being located on the front or rear sides of the pouch as shown in FIG. 9. The pouch shown in FIG. 10 also lacks the convex-shaped upper end.

Although a concave-shaped lower end is illustrated and preferred in some embodiments, the shape of the lower end of the pouch may vary widely.

The pouch is preferably knit with monofilament fiber. Preferably, the monofilament fiber has a diameter from 0.04 mm to 0.35 mm, but more preferably 0.05 to 0.2 mm. In a particularly preferred embodiment, the pouch is knit with monofilament fiber comprising P4HB or poly(butylene succinate) or copolymer thereof.

The pita pocket-shaped pouch shown in FIG. 10 may also be prepared from a tubular knit prepared as described herein, except with a lower portion that is formed by ultrasonic welding instead of knitting. Knitting is however preferred since it allows uniform stretching of the pouch.

Breast Implant Fixation Device Comprising a Pouch with Different Pore Sizes, Different Elasticities, and or Different Thicknesses of Front and Back Regions In a further embodiment, a breast implant fixation pouch device may be prepared from two or more materials with different pore sizes, two or more materials with different elasticities, or two or more materials with different thicknesses, or a combination thereof. In one embodiment, suitably shaped materials with different pore sizes, different thicknesses or both different pore sizes and different thicknesses may be joined together, for example, by sewing, gluing, or welding, in order to form a pouch for an implant. For example, two semicircular pieces 810, 820 of material may be sewn to a round piece 830 of material to form a pouch 800 for an implant as shown in FIGS. 15-17B. The pieces of material may be stitched together along the stitch lines 840 shown in FIG. 15. Alternatively, two round but different pieces of material may be stitched together, and then a cut made in one of the pieces of material to create an opening 850 in the pouch for insertion of a breast implant. The materials used to construct the pouch are preferably porous, and more preferably are textiles, including woven, non-woven, monofilament, multifilament, and knitted textiles. In a particularly preferred embodiment, the textiles are monofilament meshes, and even more preferably monofilament meshes with a Marlex knit pattern. The materials forming the pouch are preferably chosen so that the front of the pouch (which is placed just under the patient's skin) has a thickness of 0.5-10 mm, and the back of the pouch (which is placed on the chest wall of the patient) has a thickness of 0.2-0.6 mm, and more preferably from 0.2-0.4 mm. In another embodiment, the materials may be chosen so that the front of the pouch (which is placed just under the patient's skin) has an elasticity of 15-75% or 30-65%, and the back of the pouch (which is placed on the chest wall of the patient) has an elasticity of 5-25% or 8-20%, wherein the elasticity is measured as the percent increase of an area of the material when the area is subject to deformation in ASTM burst method D6797-02 using a round ball. In a particularly preferred embodiment, the materials may be chosen so that the front of the pouch has an elasticity of 30-65%, and the back of the pouch has an elasticity of 8-20%. In a further embodiment, the average pore diameters of the materials forming the pouch are selected from one or more of the following: 0.5-3 mm in the back of the pouch (which is placed on the chest wall of the patient), 0.5-1 mm in the front bottom of the pouch (where the pouch material is placed in the lower pole just under the skin of the patient), and 0.1-1 mm in the top front of the pouch (where the pouch material is placed in the upper pole just under the skin of the patient). In another embodiment, the materials used to form the pouch have one or more of the following properties: (i) burst strength of 0.1 to 30 $kgf/cm^2$; (ii) suture pullout strength of 1-7 kgf, and (iii) areal density of 40 to 190 $g/m^2$. In a particularly preferred embodiment, the pouch materials comprise poly-4-hydroxybutyrate or copolymer thereof or poly(butylene succinate) or copolymer thereof, even more preferably in the form of textiles or other porous constructs. In another embodiment, the breast implant fixation pouch device is coated with one or more of the following: a bioactive agent, antibiotic, antimicrobial, autologous fat, fat lipoaspirate, injectable fat, adipose cells, fibroblast cells, stem cells, collagen, and hyaluronic acid.

Examples of different methods to produce suitable breast implant fixation pouches with different pore sizes, different elasticities, and different thicknesses of the pouch's front and back areas are described in Examples 9-11.

IV. Methods of Implanting Pouch Containing Breast Implant to Limit Movement

The pouches containing the breast implants may be implanted in the body. Preferably, the assembly of the pouch containing the breast implant is implanted in the breast. More preferably, the pouch is implanted in a breast where the patient is seeking reconstruction or augmentation of the breast.

The breast implants are preferably placed in the pouches prior to implantation, however, the pouch may be implanted in the patient, and then the breast implant placed in the pouch. The method of securing the breast implant inside the pouch will depend upon the particular design of the pouch, and also on the breast implant. For example, in the case of the pouch of FIG. 1, the breast implant is secured inside the pouch by tightening the draw cord. Tightening the draw cord cinches the breast implant applying pressure to the implant, and limiting movement of the breast implant inside the pouch.

The pouch shown in FIGS. 4 and 6 is designed for use with tabbed breast implants that comprise one or more tabs, interlocks, or protuberances. These breast implants may be inserted into the pouch through slits in the pouch, preferably in the base of the pouch (the area of the pouch that will be in contact with the patient's chest wall). The breast implant is then oriented inside the pouch so that the tabs or protuberances on the breast implant fit through, or mate with, the slots on the pouch, as shown in FIGS. 4 and 6. Once the tabs or protuberances on the breast implant engage with the pouch, rotation and movement of the breast implant inside the pouch is limited.

In a preferred embodiment, the pouch containing the breast implant is used in breast reconstruction, particularly following mastectomy, and breast augmentation, including augmentation mastopexy. The pouch containing the breast implant may be placed in a pocket formed in the breast solely from the patient's tissues, or in a pocket that is formed using an implant, for example, a pectoralis extender, such as an acellular dermal matrix (ADM), P4HB mesh, mesh of poly(butylene succinate) or copolymer thereof, or other material that can form a hammock or sling in the breast. If desired the pocket may be formed or enlarged using a tissue expander.

In an embodiment, a procedure for implanting the pouch containing the breast implant following mastectomy comprises forming a pocket in the breast of a patient suitable for receiving the pouch containing the breast implant, and implanting the pouch containing the breast implant. In a preferred procedure for implanting the pouch containing the breast implant in a patient after mastectomy, the method of implantation comprises: (i) implanting a tissue expander in the patient; (ii) implanting a pectoralis extender in the vicinity of the tissue expander; (iii) expanding the tissue expander; (iv) removing the tissue expander; and (v) implanting the pouch containing the breast implant in the pocket created in the breast of the patient. Preferably, the pectoralis extender is sutured to the detached pectoralis major muscle, which has been mobilized in preparation for placement of a tissue expander. The suture may be either permanent or absorbable, but is preferably absorbable. Once sutured to the pectoralis major muscle, the pectoralis extender can be used as a sling or hammock to cover the inferolateral portion of an inserted tissue expander. The tissue expander may be partially inflated or uninflated prior to implantation. In the latter case, the tissue expander may be partially inflated immediately after implantation.

In an embodiment, a procedure for implanting the pouch containing the breast implant in patients desiring breast augmentation comprises implanting the pouch in the pre-pectoral position (subglandular position) to eliminate the need to detach the muscle from the chest wall, and to reduce pain associated with detachment of the muscle from the chest wall. However, in other embodiments, the pouch containing the breast implant may, if desired, be implanted in the sub-pectoral position or sub-muscular position.

Optionally, the pouch containing the breast implant may be fixated in place. In an embodiment, the pouch comprises suture straps, or similar extensions, that may be fastened to the patient's tissue. The straps may be fastened to the patient's tissue using sutures, tacks, clips, staples, or similar fastening devices. Alternatively, the pouch may be fixated in place by directly attaching the pouch to the chest wall of the patient, for example, using sutures, tacks, staples or other fastening devices and materials.

EXAMPLES

The present invention will be further understood by reference to the following non-limiting examples.

Example 1

Pouch With Draw Cord Cinch Mechanism to Limit Rotation and Movement of Breast Implant A pouch to limit rotation and movement of a breast implant with the design shown in FIG. 1 was prepared from a P4HB monofilament mesh. The mesh was knit on a 14-gauge warp knitting machine from USP size 5-0 P4HB monofilament fiber as described in Section II.G. The P4HB monofilament fiber had an elongation to break of 55%, and a weight average molecular weight of 340 kDa. After knitting, the mesh was washed and heat set at 57° C. for 5 minutes. A circular front half with a 20 cm diameter shape was cut using a die (see front half 20 of pouch implant in FIG. 2A). A circular back half 30 with a 12.5 cm diameter was also cut from the mesh with a die (see FIG. 2B). The front half 20 was further cut using a TroTec 400 laser cutter to create a pattern of rectangular holes 26 around the perimeter of the circle as shown in FIG. 2A and then the mesh was thermoformed to provide a semi-spherical 3D shape with a 0.5 cm seal area (shown as the shaded region in FIG. 2A). The P4HB mesh was molded by mounting the mesh in a three-part metal mold and thermoforming the mesh under tension in a hot water bath at 57° C. for 5 minutes. The 3D molded mesh was then quenched in a cold-water bath at 9° C. for 10 min, removed from the mold, and dried. The back half 30 circular shape, shown in FIG. 2B, was then attached to the seal region of the semi-spherical top half shape using a Brother sewing machine threaded with a USP size 6-0 P4HB monofilament fiber using a lock-stitch pattern to prevent unraveling of the stitch line. After sewing, the stitched parts were manually cut using sharp scissors to create a V-shaped slit as illustrated in FIG. 1. Finally, a draw cord 12 was threaded through the laser-cut rectangular slots in an alternating pattern as illustrated in FIG. 1.

Figure 3:
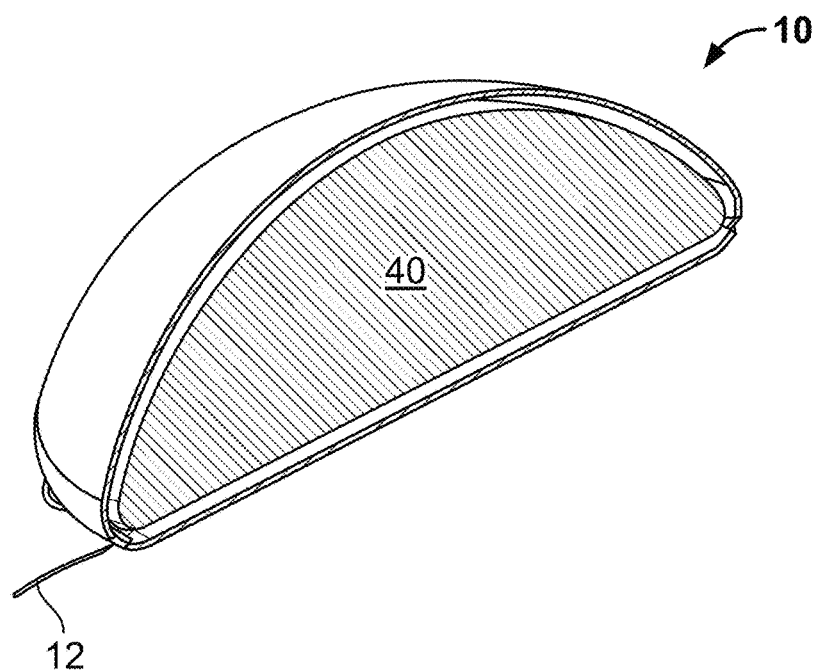
FIG. 3 is a cross-sectional view of the pouch shown in FIG. 1, with the breast implant inside the pouch, and part of the draw cord shown at the base of the pouch.

Prior to implantation, a breast implant may be inserted into the pouch through the V-shaped slit in the pouch, the draw cord pulled tight on the implant, and the draw cord fastened. The draw cord is tightened sufficiently to prevent rotation of the implant inside the pouch by more than 45 degrees, and more preferably by more than 30 degrees. FIG. 3 shows a cross-sectional diagram of the breast implant 40 inside the draw cord pouch 10 of FIG. 1.

Example 2

Pouch with Draw Cord made by Spot Welding

A pouch was formed using the same method disclosed in Example 1, except that spot welding was used to attach the two halves together to form the pouch instead of sewing. An ultrasonic spot welder with a running frequency of 20 kHz was used to spot weld the front and back halves together in the seal areas 26, 28 shown in FIGS. 2A and 2B.

Example 3

Pouch with Slits to Mate with Breast Implant Tabs

A pouch to limit rotation of a tabbed breast implant was prepared by solution spinning. FIGS. 4A, 4B illustrate a pouch 110 containing a breast implant with tabs 122 is shown in FIGS. 4A, 4B. The equipment set up used to prepare the pouch is shown in FIG. 5, and comprised a rotating collector 210, solution spinning reservoir, and a spray nozzle 220 with a 200 μm diameter orifice connected to a compressed air supply. The collector was formed in the shape of a 250-cm³ round breast implant (12 cm in diameter and 4 cm in height) from aluminum. The reservoir was filled with a filtered solution of P4HB comprising an 8% w/v solution of the polymer in chloroform. The weight average molecular weight of the P4HB polymer was 340 kDa. The polymer was solution spun onto the collector using a pump speed of 0.5 mL/min, a compressed air temperature of 22-29° C., and a pressure of 200 kPa (2 bar). The collector was rotated at 40 rpm and was placed 60 cm from the spray nozzle during solution spinning. The collector was moved during the spinning process so that an even layer of microfibers was deposited on the collector. Solution spinning under these conditions resulted in the formation of microfibers with average diameters ranging from 5 to 30 μm. Collection of the microfibers on the rotating collector was continued until a nonwoven with a thickness of 0.55 mm had been prepared. The nonwoven was then removed from the collector by cutting a V-shaped slit in the nonwoven using a sharp blade and removing the pouch from the collector mold. The sharp blade was then used to create four slots in the sides of the pouch around its perimeter at 90 degree intervals. The slots were positioned and sized to receive tabs from a mating breast implant.

Prior to implantation, a breast implant 120 with four mating tabs 122 may be inserted into the pouch through the V-shaped slit in the pouch, and the tabs of the implant passed through the slots of the pouch, as illustrated in FIGS. 4 and 6 to prevent rotation of the implant inside the pouch by more than 45 degrees, and more preferably by more than 30 degrees.

Example 4

Pouch with Slit in Base and Small Suture Straps

Figure 7:
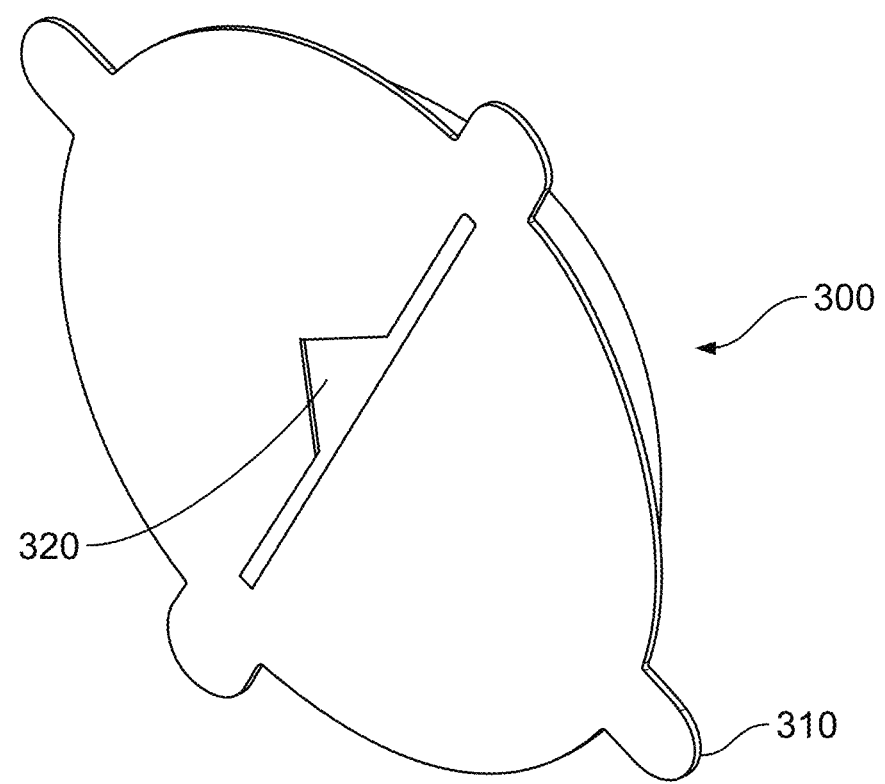
FIG. 7 shows the back of a pouch for a breast implant including a V-shape slit in the back for insertion of the breast implant, and four small suture straps placed at 90 degree intervals around the pouch perimeter in accordance with another embodiment of the invention.

A pouch 300 to limit rotation of a breast implant with small straps 310 on the outer perimeter and a V-shaped slit 320 in the rear or back, as illustrated by FIG. 7, may be prepared according to the method of Example 1, but with the following modifications. The circular back half with a 12.5 cm diameter is cut with a die, except the mesh is cut to include four small suture straps 310 placed every 90 degrees around the perimeter. A slit 320 is then made in the back half, to allow insertion of the implant into the pouch, prior to attaching the back half to the front half to form the pouch. The slit in the back eliminates the need to make the V-shaped slit 14 shown in FIG. 1.

Prior to implantation, a breast implant may be inserted into the pouch through the V-shaped slit 320 in the back of the pouch, the draw cord pulled tight on the implant, and the draw cord fastened. The draw cord is tightened sufficiently to prevent rotation of the implant inside the pouch by more than 45 degrees, and more preferably by more than 30 degrees. The pouch may be anchored to the patient's chest wall by passing sutures through the small suture straps around the perimeter of the pouch.

Modifications and variations of the methods and compositions will be apparent from the foregoing detailed description and are intended to come within the scope of the appended claims. For instance, the pouches and enclosures described herein may be shaped to snugly hold and fixate other types of implants in humans, preventing rotation and movement of the implant within the pouch, and in embodiments, delivering bioactive agents from the pouch to prevent infection.

Example 5

Pouch with Slit Made by Warp Knitting

A pouch to limit rotation of a round smooth 355 cc breast implant was made using a 24-gauge warp knitting machine equipped with a double needle bed using size 6-0 poly-4-hydroxybutyrate (P4HB) monofilament fiber (weight average molecular weight, Mw=340 kDa) and two guide bars with individual thread guide control. The pick density was set to 10 stitches per cm. The fabric was knit as a tubular construct, but wherein areas of the tube were knit together to form a pouch. FIG. 8 is a diagram showing a tubular knit 402 wherein areas of the knit tube were joined by knitting to form a pouch. The joined areas are denoted by reference numerals 410, 412. In the areas of the knit fabric that are not connected 402, the fabric is tubular and hollow inside like a hose. The pouch was knit such that the tubular hollow area consisted of closed loop stitches knit separately on the front and back bed, except for the edges 404 where the monofilament fiber was knit simultaneously on the front and back bed to form the hollow tubular structure. The connected area 410, 412 were formed by the combination of open and closed stitch knitting simultaneously on the front and back bed. The knitting displacement along the wales in the connected area was 6 loops/cm resulting in a lower semi-circular concave shape 410 as shown in FIG. 8. The knitted pattern was inverted to create an upper semi-circular convex shape 412 as shown in FIG. 8.

FIG. 9 is a figure showing a knitted pouch 400. The dimensions of the pouch were 11 cm wide by 11 cm tall and 0.65 mm thickness (including both layers of the pouch). An area (440) extends outwards from the connected area (knitted closure) 430. The extension region was formed during knitting, and may be used for fixation of the pouch to tissue during implantation to limit movement of the pouch and breast implant. Additionally, as shown in FIG. 9, a 6 cm wide slit 450 was cut on one side of the tubular area of the knit pouch to create an opening for insertion of a breast implant. The side that the slit is cut is preferably placed against the chest wall of the patient as discussed above.

Example 6

Pouch with Slit Made by Warp Knitting and Ultrasonic Welding

A pouch to limit rotation of a breast implant may be made using a warp knitting machine to produce a tubular structure as described in Example 5, but without forming the connected areas shown in FIG. 8. The connected areas shown in FIG. 8 may be formed instead using an ultrasonic welder to form semi-circular heat seals between the layers of warp knit. The heat seals so formed create a pouch in the tubular structure for the implant. A slit may be introduced in the tubular knit for introduction of the breast implant in the same manner as described in Example 5.

Example 7

Figures 11A, 11B:
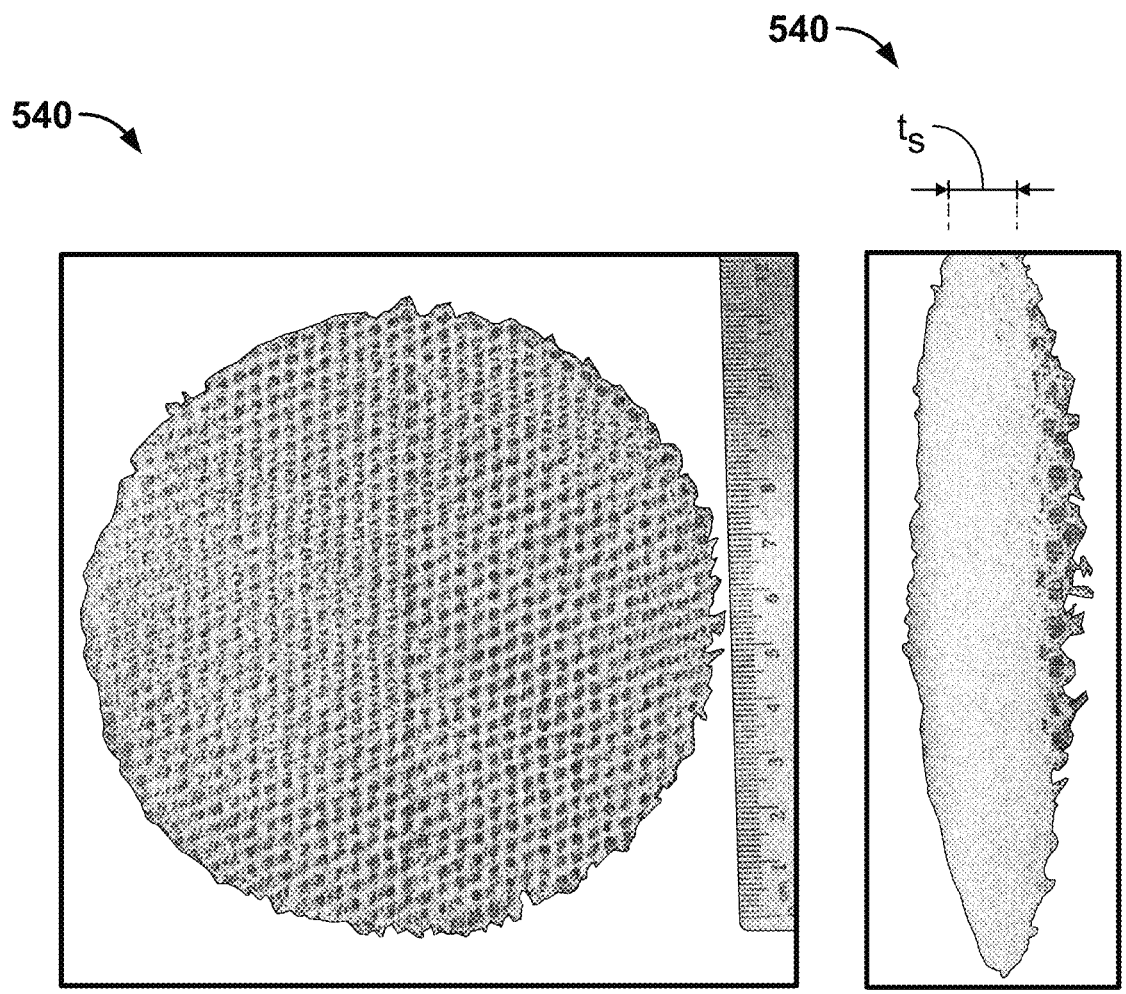
FIG. 11A shows a spacer mesh with a honey comb knit pattern for use in fabricating an implant breast fixation device in accordance with an embodiment of the invention.
FIG. 11B is a side view of the breast implant fixation pouch device shown in FIG. 11A.

Self-Gripping Resorbable Breast Implant Pouch Made from Circular Cut Warp Knit Mesh In this example, a pouch for a breast implant was made from a spacer mesh that was produced on a 20-gauge double needle bed warp knitting machine using 120-micron diameter P4HB monofilament fiber with a weight average molecular weight of 320 kDa. With reference to FIGS. 11A, 11B, a spacer mesh 540 was made using a honey comb knitting pattern design on both the front and back needle beds (see FIG. 11A). We observed that this allows for good drapability of the pouch around a spherical breast implant. The knitted spacer mesh 540 had two distinctive pore sizes, 0.1 (small) and 9 mm$^2$ (large), a thickness ($t_s$) of 7 mm (distance between front and back faces of the mesh shown in FIG. 11B), and an areal density of 176 g/m$^2$. The spacer mesh was then cut into 10 to 15 cm circles (FIG. 11A) to accommodate smooth round breast implants with volumes of 255 cc to 650 cc.

Figure 12A:
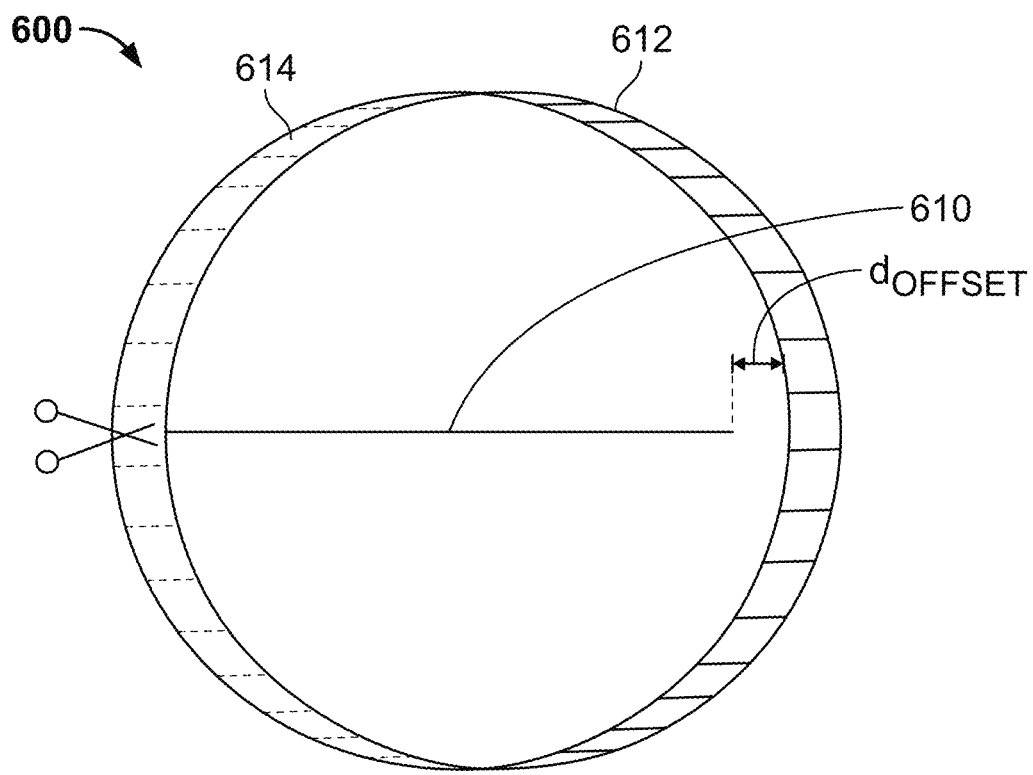
FIG. 12A is a diagram showing the position and length of a slit made in a spacer mesh, such as that shown in FIG. 11A, during the preparation of a breast implant fixation pouch device.

With reference to FIG. 12A, a slit 610 to allow insertion of a breast implant into the pouch was made on only the first face 612 of the spacer mesh 600 using scissors and an offset distance ($d_{offset}$) from each edge. In embodiments, the offset distance ranges from 3-8 mm, 4-6 mm, and in some embodiments is about 5 mm.

Figure 12B:
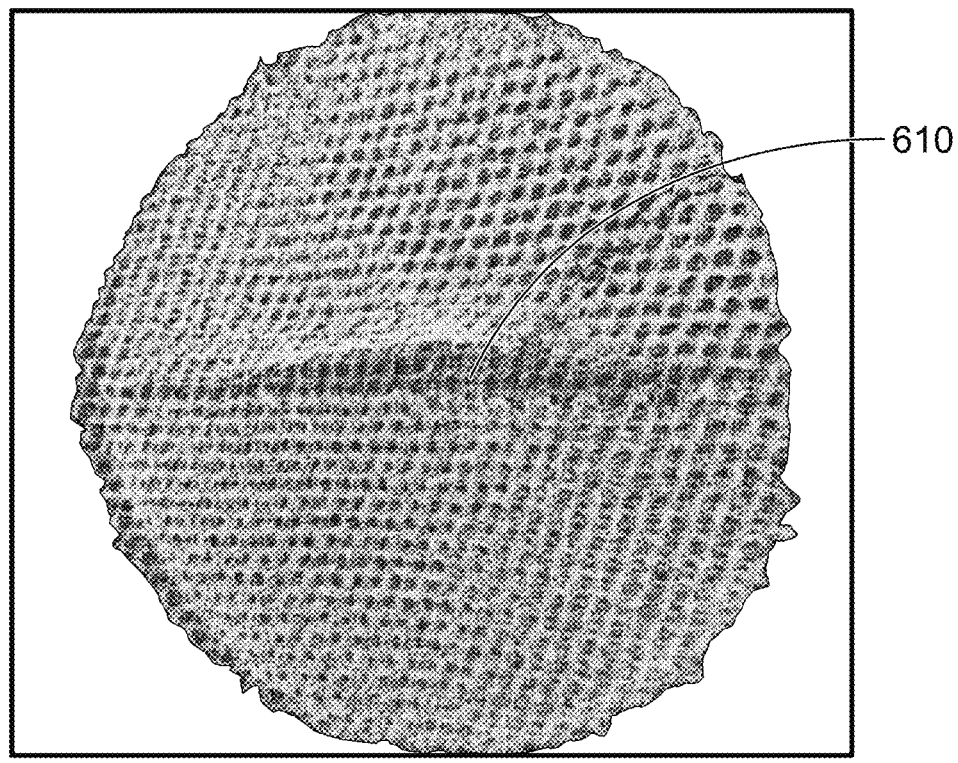
FIG. 12B depicts a spacer mesh including a slit in accordance with an embodiment of the invention used in the preparation of a breast implant fixation pouch device.

The pouch 600 after cutting a slit 610 is shown in FIG. 12B.

Figure 13A:
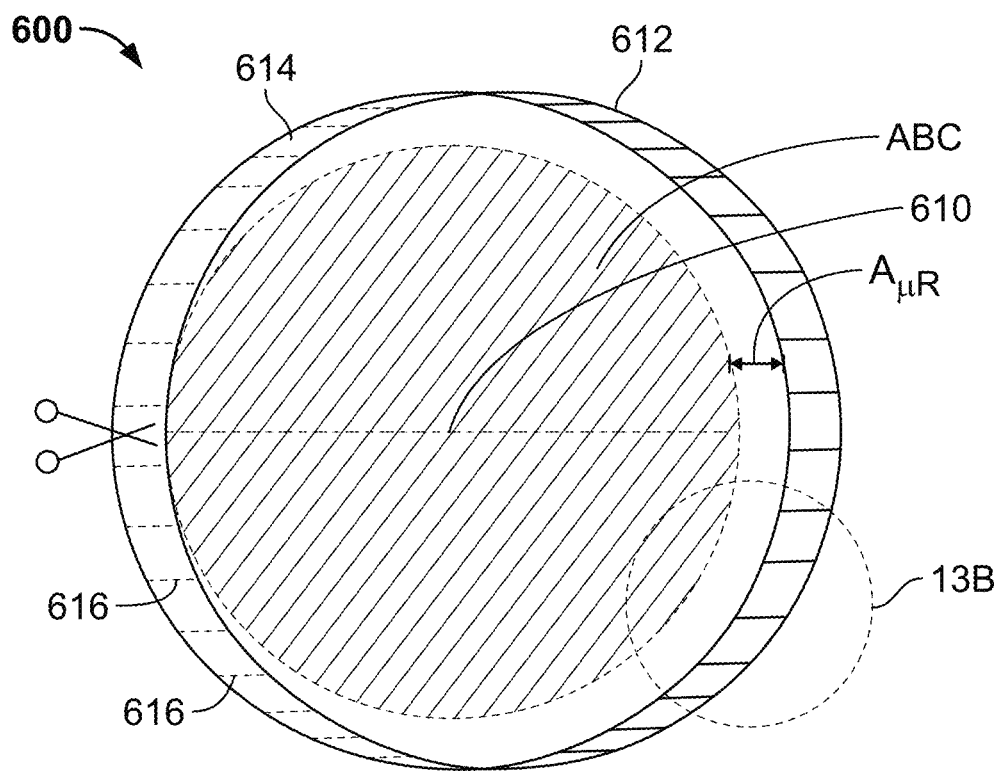
FIG. 13A depicts a spacer fabric that is cut to separate the front and back faces of a spacer mesh during the manufacture of a breast implant fixation pouch device in accordance with an embodiment of the invention.

With reference to FIG. 13A, the interlaced P4HB monofilaments 616 connecting the front face 612 and back face 614 of the spacer mesh were cut using a hot knife at 85° C. in the mid-plane (ABC) between the front and back faces of the meshes, while leaving a 5 mm intact (uncut) region ($A_{ur}$) along the periphery (as illustrated in FIG. 13A), to create a pocket for the breast implant.

Figure 13B:
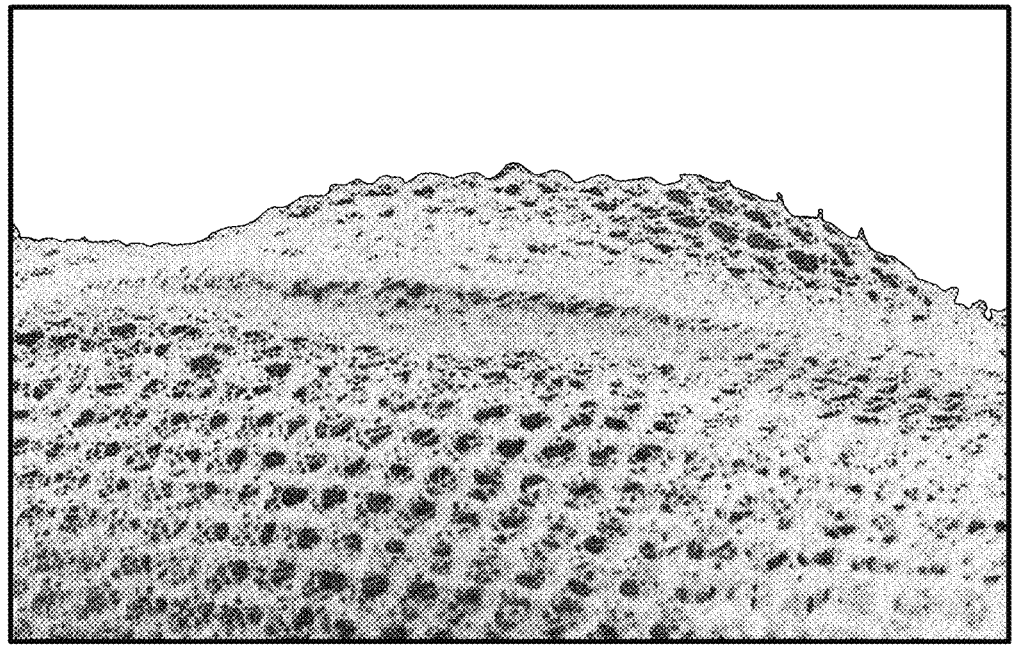
FIG. 13B is an enlarged view of the cut spacer fabric depicted in FIG. 13A in accordance with an embodiment of the invention.

FIG. 13B shows an enlarged view of a portion of the spacer fabric after it has been cut as described above.

Figure 14:
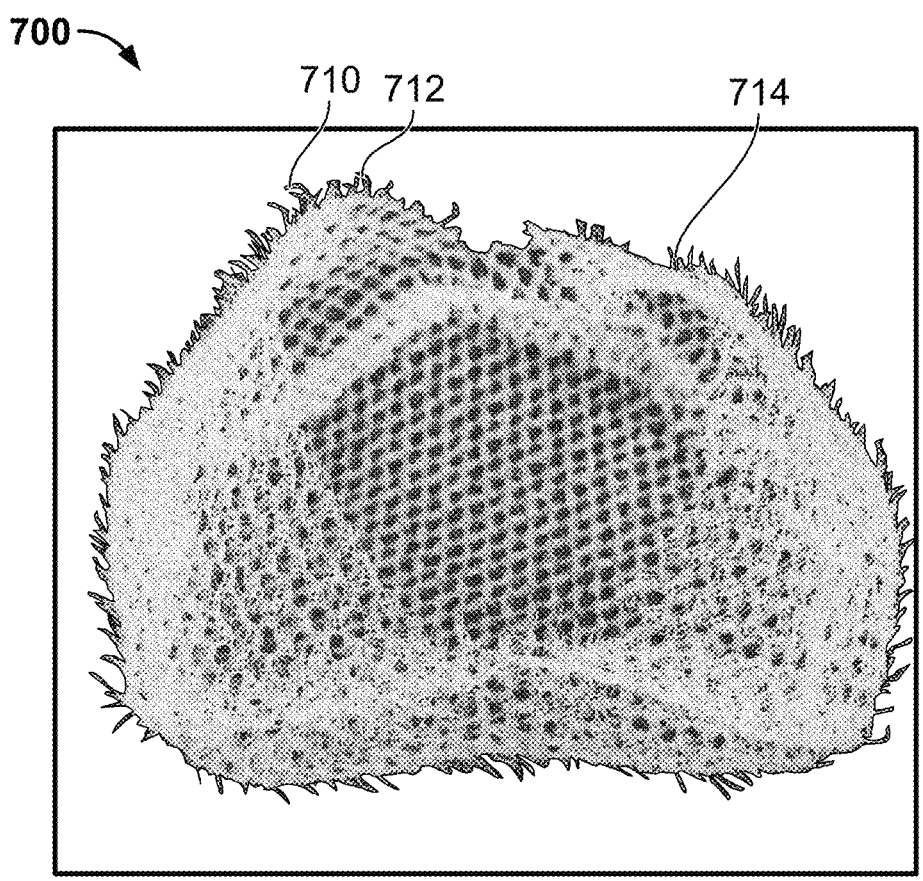
FIG. 14 is a figure of a breast implant fixation pouch formed from a spacer mesh by cutting the internal connecting fibers in the midplane region between the front and back faces of the spacer mesh (as illustrated in FIG. 13A), and flipping the construct inside-out to form a self-gripping pouch for a breast implant with fibers exposed as tissue anchors on the outer surface of the pouch in accordance with an embodiment of the invention.

Next, and with reference to FIG. 14, the precursor pouch or pocket of FIG. 13A was flipped inside-out resulting in a self-gripping pouch 700 where cut monofilaments 710, 712, 714 . . . were exposed on the outer surface of the pouch as tissue anchors. The cut monofilaments 710, 712, 714, . . . protruded on average 3 mm away from either face of the mesh. The density of anchors was on average 26 anchors/cm$^2$ of mesh. The protruding anchors may range in length from 1-10 mm, and more preferably are about 2-4 mm, and in some variations 1-3 mm.

Example 8

Drapable Lightweight Breast Implant Pouch Made Using Overlock Stitch

Figure 17A:
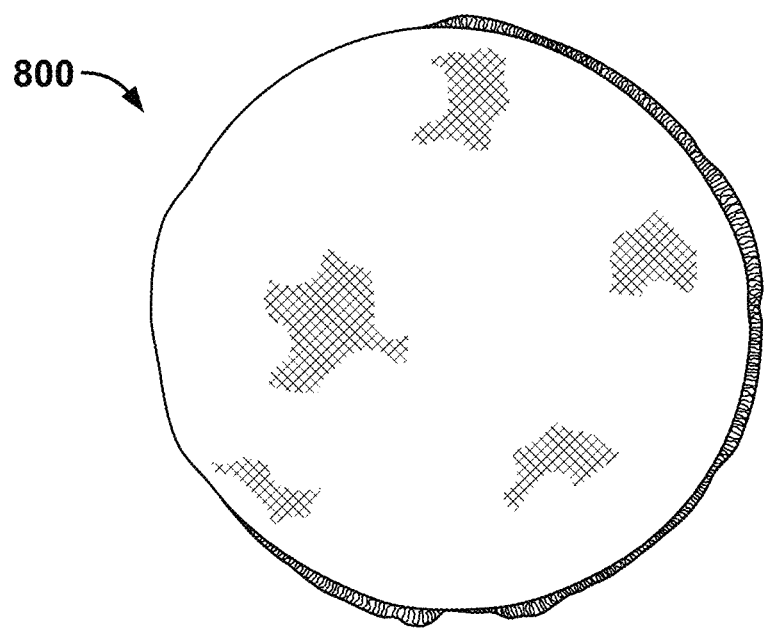
FIG. 17A shows the front of a breast implant fixation pouch, manufactured as shown in FIG. 15, with a breast implant inserted therein in accordance with an embodiment of the invention.
Figure 17B:
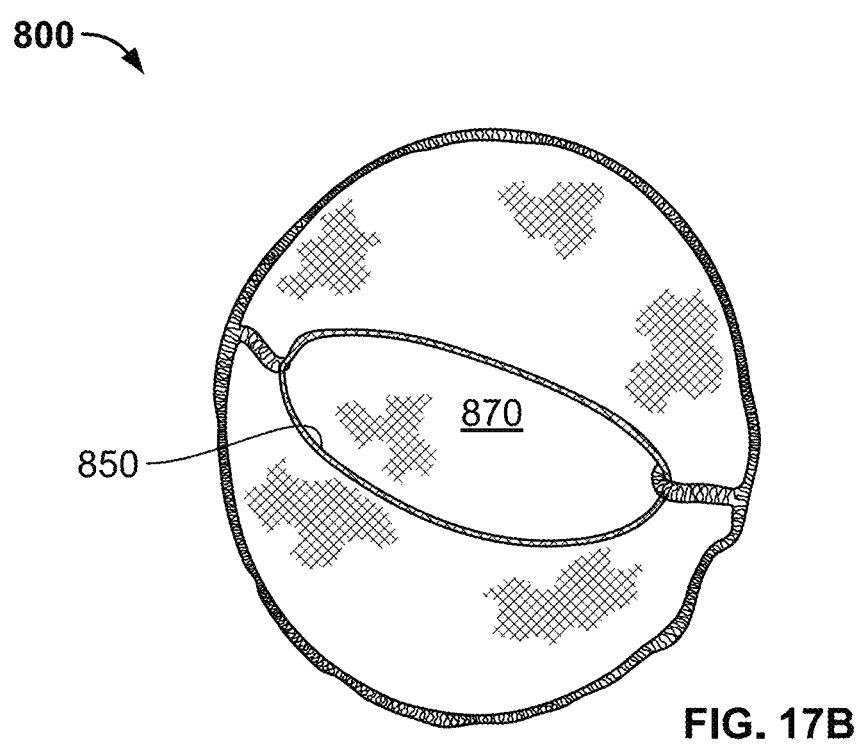
FIG. 17B shows the back of a breast implant fixation pouch, manufactured as shown in FIG. 15, with a breast implant inserted therein in accordance with an embodiment of the invention.

With reference to FIGS. 15 to 17B, a resorbable pouch for a breast implant was made from a 14-gauge Marlex mesh knit pattern using 100-micron diameter P4HB monofilament with a weight average molecular weight of 310 kDa. The average areal density of the mesh was 48 g/m$^2$. The mesh was cut into three parts: two semicircles of 11 cm radius (810 and 820) and a full circle of 16 cm diameter (830). The pouch was assembled by placing the semicircle 810 and semicircle 820 side by side on top of the full circular cutout (830), and stitched with a 1 cm overlap between semicircle 810 and semicircle 820 and the full circular cutout (830) along the stitch lines 840 using an overlock stitch consisting of three separately fed P4HB monofilaments with 2 grams of tension on each. The stitched edge 850 of the pouch is shown in FIG. 16A, and a diagram of the stitch pattern 860 is shown in FIG. 16B. The stitched assembly formed a hemispherical pouch 800 with full circular cutout (830) being the front half of the pouch and (810) and (820) forming the back half of the pouch with a middle opening 850 for insertion of a breast implant. The front of the pouch 800 with a breast implant inserted is shown in FIG. 17A, and the back of the pouch 800 with a breast implant 870 inserted therein is shown in FIG. 17B.

Example 9

Breast Implant Fixation Device Comprising a Pouch with Varying Pore Size and Thickness Assembled with Overlock Stitch A resorbable pouch for breast implants was made from two types of knit meshes: mesh (M1) consisting of 14-gauge Marlex knit pattern made with 168-micron diameter P4HB monofilament (90% elongation) and an average areal density of 152 g/m$^2$; and mesh (M2) consisting of 14-gauge Marlex knit pattern made with 120-micron diameter P4HB monofilament (25% elongation) and an areal density of 48 g/m$^2$. Both monofilaments had an average molecular weight of 310 kDa. Mesh (M1) was not heat set while mesh (M2) was heat set at 54° C. for 5 min leading respectively to percent elasticities under ball burst of 42% and 18%, thicknesses of 0.75 mm and 0.38 mm, and average major pore diameter sizes of 0.35 and 0.42 mm.

A drapable breast implant fixation device was prepared by forming a pouch from the two meshes, M1 and M2. The pouch was constructed from three parts: two semicircular pieces of mesh M2 of 11 cm radius (shown as 810 and 820 in FIG. 15) and a round piece of mesh M1 of 16 cm diameter (shown as 830 in FIG. 15). The semicircular pieces were placed side by side on the round cutout with a 1 cm overlap as shown in FIG. 15, and stitched together using an overlock stitch (as shown in FIG. 16B) consisting of three separately fed 100-micron P4HB monofilaments with 2 grams of tension on each. The stitched assembly formed a hemispherical pouch with 830 being the front half of the pouch with a thickness of 0.75 mm, pore size of 0.35 mm, and elasticity of 42%, and (810) and (820) forming the back half of the pouch with a thickness of 0.38 mm, pore size of 0.42 mm, elasticity of 18%, and a middle opening on the bottom half for insertion of a breast implant.

Example 10

Breast Implant Fixation Device Comprising a Pouch with Varying Pore Size and Thickness Assembled with Ultrasonic Welding In this example, a breast implant fixation device 880 was prepared as described in Example 9, except that the pouch was formed by ultrasonically welding the meshes 810 and 820 to mesh 830 using a 1 mm wide rotary horn set at a 20 kHz frequency, 45 microns amplitude, and 48 psi pressure.

Example 11

Figure 18:
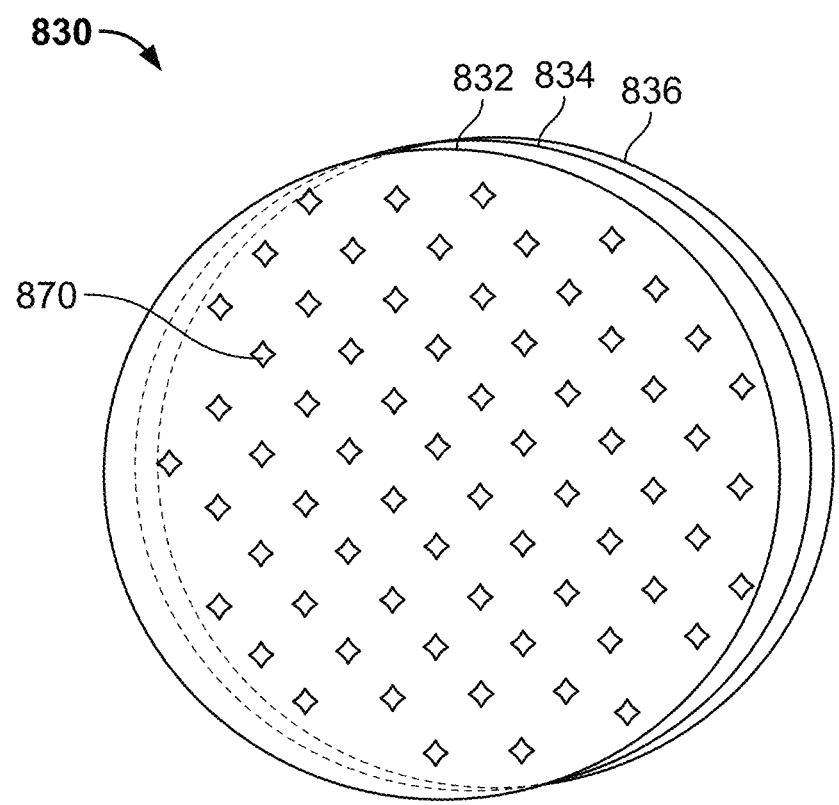
FIG. 18 is a diagram showing three round meshes pre-assembled together to produce an enhanced front mesh of a breast implant pouch in accordance with an embodiment of the invention.

Breast Implant Fixation Device Comprising a Pouch with Varying Pore Size and Thickness Assembled with Ultrasonic Welding In this example, a resorbable pouch for fixation of breast implants was prepared as described in Example 10, except that front face 830' was prepared by ultrasonically welding together, at discrete points 870 evenly spaced in a 2 cm diamond pattern as shown in FIG. 18, three pre-cut round pieces of mesh 832, 834, 836. Welding of the three round pieces of mesh resulted in the front half of the pouch having a thickness of 2.25 mm.

We claim:

1. A breast implant fixation device to limit migration of a breast implant in a patient comprising:
   a pouch comprising a shape and size to at least partially cover the breast implant;
   a plurality of pores for tissue to grow therein and secure the device to the patient;
   wherein the pouch comprises a back area for placement on the chest wall of the patient, a front area opposite the back area, the front area comprising a front bottom for placement in the lower pole of the breast, a front top for placement in the upper pole of the breast, and a front intermediate-region for placement under the skin of the patient; wherein at least a portion of the front area of the pouch is thicker than an opposed back area of the pouch; and wherein the back area includes a back top opposite the front top, a back intermediate-region opposite the front intermediate-region, and a back bottom opposite the front bottom;
   wherein a portion of the back area has an elasticity that is lower than an elasticity of the opposed portion of the front area.

2. The device of claim 1, wherein the thickness of the front area of the pouch prevents the breast implant from being palpable, or to hide any ripples or indentations in the skin of the patient, when a breast implant is placed in the pouch, and the pouch is implanted in the breast of the patient.

3. The device of claim 1, wherein the front area of the pouch has an elasticity range of 30-65%, wherein the elasticity is measured as the percent increase in an area when an area is subject to deformation in ASTM burst method D6797-02 using a round ball.

4. The device of claim 1, wherein the back area of the pouch has an elasticity range of 8-20%, wherein the elasticity is measured as the percent increase in an area when an area is subject to deformation in ASTM burst method D6797-02 using a round ball.

5. The device of claim 1, wherein the pouch has at least one of the following thicknesses: a thickness of the front area of the pouch between 0.75-3 mm, and a thickness of the back area of the pouch between 0.2-0.4 mm.

6. A breast implant fixation device to limit migration of a breast implant in a patient comprising:
  a pouch comprising a shape and size to at least partially cover the breast implant;
  a plurality of pores for tissue to grow therein, securing the device to the patient anatomy;
  wherein the pouch comprises a back area for placement on the chest wall of the patient, a front area opposite the back area, the front area comprising a front bottom for placement in the lower pole of the breast, a front top for placement in the upper pole of the breast, and a front intermediate-region for placement under the skin of the patient; and
  wherein the back area includes a back top opposite the front top, a back intermediate-region opposite the front intermediate-region, and a back bottom opposite the front bottom; and wherein a portion of the back area has a different elasticity than an opposed portion of the front area;
  wherein the elasticity of the portion of the back area is lower than the elasticity of the opposed portion of the front area.

7. The device of claim 6, wherein the opposed portion of the front area of the pouch has an elasticity of 30-65%, wherein the elasticity is measured as the percent increase of the area when the area is subject to deformation in ASTM burst method D6797-02 using a round ball.

8. The device of claim 7, wherein the portion of the back area of the pouch has an elasticity of 8-20%, wherein the elasticity is measured as the percent increase of the area when the area is subject to deformation in ASTM burst method D6797-02 using a round ball.

9. The device of claim 6, wherein the pouch is shaped to enclose a breast implant.

10. The device of claim 6, wherein the pouch comprises at least one seam connecting the back area of the pouch with the front intermediate-region, front top or front bottom of the pouch.

11. The device of claim 6, wherein the pouch has one or more of the following pore sizes: an average pore diameter in the back area of the pouch between 0.5 mm and 3 mm, an average pore diameter in the front bottom of the pouch between 0.5 mm and 1 mm, and an average pore diameter in the front top of the pouch between 0.1 mm and 1 mm.

12. The device of claim 6, wherein the pouch comprises one or more of the following: a textile, woven textile, non-woven textile, monofilament mesh, or multifilament mesh.

13. The device of claim 12, wherein the textile, woven textile, non-woven textile, monofilament mesh, or multifilament mesh has at least one of the following properties: (i) burst strength of 0.1 to 30 kgf/cm2; (ii) suture pullout strength of 1 to 7 kgf; and (iii) areal density of 40 to 190 g/m2.

14. The device of claim 6, wherein the back area of the pouch comprises a slit or opening to allow insertion of the breast implant into the pouch.

15. The device of claim 6, wherein the pouch further comprises one or more of the following: a draw cord, a securing element to maintain the breast implant in fixed alignment with the pouch, and a slot or receptacle to engage a protuberance from a breast implant.

16. The device of claim 6, wherein the pouch comprises a resorbable polymer.

17. The device of claim 16, wherein the resorbable polymer is poly-4-hydroxybutyrate or copolymer thereof, or poly(butylene succinate) or copolymer thereof.

18. The device of claim 6, wherein the pouch further comprises one or more of the following: an additive, bioactive agent, antibiotic, antimicrobial, autologous fat, fat lipoaspirate, injectable fat, adipose cells, fibroblast cells, stem cells, collagen, and hyaluronic acid.

19. The device of claim 6, wherein an endotoxin content of the device is less than 20 endotoxin units, and the device is sterile.

20. The device of claim 6, wherein the thickness of the front area of the pouch decreases from the front top to the front bottom.

21. The device of claim 6, wherein the elasticity of the front area of the pouch increases from the front top to the front bottom.

* * * * *